(12) United States Patent
Fontaine et al.

(10) Patent No.: US 9,856,194 B2
(45) Date of Patent: Jan. 2, 2018

(54) CATALYSTS FOR THE PRODUCTION OF METHANOL FROM CARBON DIOXIDE

(71) Applicant: UNIVERSITÉ LAVAL, Quebec (CA)

(72) Inventors: Frédéric-Georges Fontaine, Quebec (CA); Marc-André Courtemanche, Quebec (CA)

(73) Assignee: Université Laval, Québec, Québec (CA)

( * ) Notice: Subject to any disclaimer, the term of this patent is extended or adjusted under 35 U.S.C. 154(b) by 0 days.

(21) Appl. No.: 14/259,733

(22) Filed: Apr. 23, 2014

(65) Prior Publication Data

US 2014/0350303 A1   Nov. 27, 2014

Related U.S. Application Data

(60) Provisional application No. 61/815,066, filed on Apr. 23, 2013.

(51) Int. Cl.
*C07C 29/09* (2006.01)
*C07F 5/02* (2006.01)
*B01J 31/24* (2006.01)
*B01J 31/02* (2006.01)
*B01J 31/14* (2006.01)

(52) U.S. Cl.
CPC .......... *C07C 29/09* (2013.01); *B01J 31/0215* (2013.01); *B01J 31/0237* (2013.01); *B01J 31/0267* (2013.01); *B01J 31/146* (2013.01); *B01J 2231/625* (2013.01); *Y02P 20/52* (2015.11)

(58) Field of Classification Search
CPC ...... C07C 29/09; C07F 5/027; B01J 31/2404; B01J 2231/625
See application file for complete search history.

(56) References Cited

PUBLICATIONS

Gloaguen et al., Journal of the American Chemical Society, (2011), 133(43), p. 17232-17238.*
Porcel et al., Angew. Chem. Int. Ed. (2010), vol. 49, p. 6186-6189.*
Sircoglou et al., Angew. Chem. Int. Ed., (2007), 46, p. 8583-8586.*

(Continued)

*Primary Examiner* — Yong Chu
(74) *Attorney, Agent, or Firm* — Parker Highlander PLLC

(57) ABSTRACT

Catalysts for the reduction of $CO_2$ are described herein. More specifically, catalysts of Formula I and Formula II:

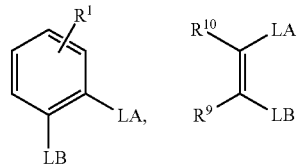

wherein LB is a Lewis base; LA is a Lewis acid; $R^1$ is selected from hydrogen, alkyl, substituted alkyl, cycloalkyl, substituted cycloalkyl, phenyl and substituted phenyl; and $R^9$ and $R^{10}$ are independently selected from alkyl, substituted alkyl, cycloalkyl, substituted cycloalkyl, phenyl and substituted phenyl; are described. A process for the production of methanol from $CO_2$ using such catalysts is also described.

9 Claims, 4 Drawing Sheets

(56) References Cited

PUBLICATIONS

Balueva et al., Inst. Org. Fiz. Khim. Im. Arbuzova, Kazan, USSR Izvestiya Akademii Nauk SSSR, Seriya Khimicheskaya (1991), 10, p. 2397-2400 (Abstract from STN search report with chemical structure).*

Gott et al., Organometallics, (2011), 30(16), p. 4236-4249.*

Appelt et al., << Geminal phosphorus/aluminum-based frustrated Lewis pairs: C—H versus C≡C activation and CO2 fixation >>, Angew. Chem. Int. Ed., 50, 3925-3928, 2011.

Ashley et al., << Non-metal-mediated homogeneous hydrogenation of CO2 to CH3OH >>, Angew. Chem., Int. Ed., 48, 9839-9843, 2009.

Balaraman et al., << Efficient hydrogenation of organic carbonates, carbamates and formates indicates alternative routes to methanol based on CO2 and CO >>, Nature Chemistry, vol. 3, 609-614, 2011.

Basle et al., << Phosphine-boronates : efficient bifunctional organocatalysts for Michael addition >>, Chem. Commun., 48, 4495-4497, 2012.

Berkefeld et al., << Tandem frustrated Lewis pair/tris(pentafluorophenyl)borane-catalyzed deoxygenative hydrosilylation of carbon dioxide >>, J. American Chemical Society, 132, 10660-10661, 2010.

Berkefeld et al., Decamethylscandocinium-hydrido-(perfluorophenyl)-borate : fixation and tandem tris(perfluorophenyl)-borane catalysed deoxygenative hydrosilation of carbon dioxide >>, Chem. Sci., 4, 2152-2162, 2013.

Bontemps et al., << On the versatile and unusual coordination behavior of ambiphilic ligands o-R2P(Ph)BR'2 >>, Journal of American Chemical Society, vol. 128, 12056-12057, 2006.

Bontemps et al., << Bridging M—Cl bonds with ambiphilic phosphine-borane ligands >>, Chem. Asian J., vol. 4, 428-435, 2009.

Bontemps et al., << Borane-mediated carbon dioxide reduction at ruthenium: formation of C1 and C2 compounds >>, Angew. Chem. Int. Ed., 51, 1671-1674, 2012.

Boudreau et al., << Reactivity of Lewis pairs (R2PCH2AlMe2)2 with carbon dioxide >>, Chem. Commun, 47, 11131-11133, 2011.

Chakraborty et al., << An efficient nickel catalyst for the reduction of carbon dioxide with a borane >>, Journal of American Chemical Society, vol. 132, 8872-8873, 2010.

Chakraborty et al., << Catalytic properties of nickel bis(phosphinite) pincer complexes in the reduction of CO2 to methanol derivatives >>, Polyhedron, 32, 30-34, 2012.

Eisenschmid et al., << The iridium complex catalyzed reduction of carbon dioxide to methoxide by alkylsilanes >>, Organometallics, vol. 8, 1822-1824, 1989.

Huang et al., << The catalytic role of N-heterocyclic carbene in a metal-free conversion of carbon dioxide into methanol: a computational mechanism study >>, Journal of American Chemical Society, vol. 132, 12388-12396, 2010.

Huang et al., << How does the nickel pincer complex catalyze the conversion of CO2 to a methanol derivative? A computational mechanistic study >>, Inorganic Chemistry, 50, 3816-3825, 2011.

Huff et al., << Cascade catalysis for the homogeneous hydrogenation of CO2 to methanol >>, Journal of the American Chemical Society, 133, 18122-18125, 2011.

Khandelwal et al., << Deoxygenierende reduktion von kohlendioxid zu methan, toluol und diphenylmethan mit [Et2Al]+ als katalysator >>, Angew. Chem., 124, 7435-7439, 2012. (English abstract of German publication).

Lalrempuia et al., << Effective fixation of CO2 by iridium-catalyzed hydrosilylation >>, Angew. Chem. Int. Ed., 51, 12824-12827, 2012.

Matsuo et al., << From carbon dioxide to methane: homogeneous reduction of carbon dioxide with hydrosilanes catalyzed by zirconium-borane complexes >>, Journal of American Chemical Society, vol. 128, 12362-12363, 2006.

Menard et al., << Room temperature reduction of CO2 to methanol by al-based frustrated Lewis pairs and ammonia borane >>, Journal of the American Chemical Society, vol. 132, 1796-1797, 2010.

Mitton et al., << Mild reduction of carbon dioxide to methane with tertiary silanes catalyzed by platinum and palladium silyl pincer complexes >>, Chemistry European Journal, 48, 15258-15262, 2012.

Mömming et al., << Reversible metal-free carbon dioxide binding by frustrated Lewis pairs >>, Angew. Chem. Int. Ed., 48, 6643-6646, 2009.

Park et al., << An efficient iridium catalyst for reduction of carbon dioxide to methane with trialkylsilanes >>, Journal of the American Chemical Society, 134, 11404-11407, 2012.

Porcel et al., << Reaction of singlet dioxygen with phosphine-borane derivatives: from transient phosphine peroxides to crystalline peroxoboronates >>, Angew. Chem. Int. Ed., 49, 6186, 2010.

Riduan et al., << Conversion of carbon dioxide into methanol with silanes over N-heterocyclic carbene catalysts >>, Angew. Chem. Int. Ed., 48, 3322-3325, 2009.

Roters et al., << Dimeric aluminum-phosphorus compound as masked frustrated Lewis pairs for small molecule activation >>, Dalton Transactions, 41, 9033, 2012.

Schäfer et al., << Silyl cation mediated conversion of CO2 into benzoic acid, formic acid, and methanol >>, Angew. Chem. Int. Ed., 51, 2981-2984, 2012.

Theuergarten et al., << Fixation of carbon dioxide and related small molecules by a bifunctional frustrated pyrazolylborane Lewis pair >>, Dalton Transactions, 41, 9101, 2012.

Tominaga et al., << Ruthenium complex catalysed hydrogenation of carbon dioxide to carbon monoxide, methanol and methane >>, Chem. Soc., Chem. Commun., 629-631, 1993.

Wesselbaum et al., << Hydrogenation of carbon dioxide to methanol by using a homogeneous ruthenium-phosphine catalyst >>, Angew. Chem. Int. Ed., 51, 7499-7502, 2012.

* cited by examiner

CATALYSTS FOR THE PRODUCTION OF METHANOL FROM CARBON DIOXIDE

CROSS-REFERENCE TO RELATED APPLICATIONS

The present application claims the benefit of priority from U.S. Provisional Application No. 61/815,066 filed on Apr. 23, 2013. The entire text of the above-referenced disclosure is specifically incorporated herein by reference.

FIELD

The present disclosure broadly relates to the production of methanol. More specifically but not exclusively, the present disclosure relates to catalysts for the production of methanol from carbon dioxide. The present disclosure also relates to a process for the production of methanol from carbon dioxide using such catalysts.

BACKGROUND

It is widely known that carbon dioxide is a green-house gas and considered one of the most important contributors to global warming. Many initiatives have been put forward by a great number of countries with the aim of reducing carbon dioxide emissions. The transformation of carbon dioxide into valuable chemicals, such as energy vectors like methane or methanol, is a highly desirable objective having received considerable interest in recent years. Most of the current systems capable of catalyzing the reduction of $CO_2$ into valuable products, including notably the inverse water-gas shift reaction to generate carbon monoxide which in turn can be transformed into several useful chemicals, call upon the use of transition metals.[1-5]

Recently, some organometallic systems have shown promise in generating valuable chemicals in one pot under mild conditions. For example, Milstein described a ruthenium pincer complex to reduce $CO_2$-derived carbamates, carbonates and formates to methanol using $H_2$ as a hydrogen source.[6]

Methanol has also been obtained from $CO_2$ and $H_2$ by an elegant cascade reaction using ruthenium and scandium catalysts.[5b] The most active systems to date for the reduction of $CO_2$ into high hydrogen content molecules include a ruthenium phosphine complex and a nickel pincer complex.[5c, 4a] An iridium catalyst has recently been described that can reduce $CO_2$ into methane with a Turn-Over Number (TON) ranging up to 8300.[2]

Recently, a variety of transition metal-free systems have emerged for carbon dioxide activation. Lewis acidic $Et_2Al^+$ species were shown to catalytically reduce carbon dioxide to methane.[7b] Similarly, silyl cations were shown to catalytically reduce $CO_2$ to a mixture of benzoic acid, formic acid and methanol.[8c] However, both systems greatly lack selectivity and generate undesirable alkylation by-products.

An interesting alternative for carbon dioxide activation is the use of "frustrated Lewis pairs" (FLP).[9a] Since its initial discovery, many ambiphilic systems have been shown to be active in the stoichiometric fixation of $CO_2$.[9b-e] Piers demonstrated an elegant use of this concept for the catalytic reduction of $CO_2$ into methane using the robust TMP/B $(C_6F_5)_3$ (TMP=2,2,6,6-tetramethylpiperidine) system in association with $Et_3SiH$, albeit with limited turnover numbers.[7a] The FLP system consisting of $PMes_3/AlX_3$ (X=Cl, Br) has also been shown to not only bind $CO_2$ but also to reduce it to methanol by hydrolysis.[10a] O'Hare and Ashley also demonstrated that $CO_2$ could be hydrogenated using TMP/B $(C_6F_5)_3$.[10b] Unfortunately, these systems require stoichiometric amounts of FLP.

Some of the limitations in the $CO_2$ activation by FLP systems include the generation of stable intermediates that limit the catalytic efficiency of the system as well as the deactivation of the catalytic system by the products generated. Although interesting in concept, none of the FLP or ambiphilic systems reported to date demonstrate efficient catalytic activity for carbon dioxide reduction.

The only efficient organocatalytic system reported to date for the reduction of $CO_2$ into methanol uses highly Lewis basic N-heterocyclic carbene catalysts in combination with diphenylsilane as the hydrogen source with turn-over frequencies (TOF) of 25 $h^{-1}$ at 25° C.[8a]

Ambiphilic systems with little "frustrated" character and/or weak Lewis acidity and basicity have recently been investigated.[9b] Among those, aryl bridged phosphine-boranes have been extensively studied by Bourissou.[11] These compounds were shown to be quite robust, stable and readily synthesized. Their use in the activation of singlet oxygen and as organocatalysts for Michael addition reactions has recently been disclosed.[12,13]

The present disclosure refers to a number of documents, the contents of which are herein incorporated by reference in their entirety.

SUMMARY

The present disclosure broadly relates to the production of methanol by catalytic reduction of $CO_2$. In one aspect, the present disclosure relates to catalysts for the production of methanol from carbon dioxide. In an embodiment of the present disclosure, the catalysts comprise a frustrated Lewis pair. In a further aspect, the present disclosure relates to a process for the production of methanol from $CO_2$ using such catalysts. In a further aspect, the present disclosure relates to a catalytic composition for the production of methanol from carbon dioxide.

In an embodiment, the present disclosure includes a catalyst of Formula I:

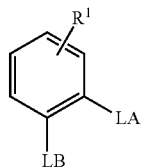

Formula I wherein:
LB is a Lewis base;
LA is a Lewis acid; and
$R^1$ is selected from hydrogen, alkyl, substituted alkyl, cycloalkyl, substituted cycloalkyl, phenyl and substituted phenyl.

In an embodiment, the catalyst of Formula I is:

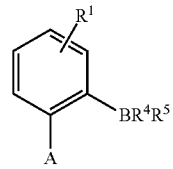

wherein:

A is selected from $PR^2R^3$, $NR^2R^3$ and $SR^2$;

$R^1$ is selected from hydrogen, alkyl, substituted alkyl, cycloalkyl, substituted cycloalkyl, phenyl and substituted phenyl;

$R^2$ and $R^3$ are independently selected from alkyl, substituted alkyl, cycloalkyl, substituted cycloalkyl, phenyl and substituted phenyl;

$R^4$ and $R^5$ are independently selected from hydrogen, alkyl, substituted alkyl, cycloalkyl, substituted cycloalkyl, phenyl, substituted phenyl, $OR^6$ and $NR^7R^8$; or $R^4$ and $R^5$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^6$ is alkyl or substituted alkyl; and $R^7$ and $R^8$ are independently selected from hydrogen, alkyl, substituted alkyl, cycloalkyl, substituted cycloalkyl, phenyl and substituted phenyl.

In an embodiment, $R^1$ is hydrogen.

In an embodiment, $R^1$ is selected from $C_{1-10}$-alkyl. In a further embodiment, $R^1$ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^1$ is selected from $C_{1-5}$-alkyl. In a further embodiment, $R^1$ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^1$ is selected from $C_{3-7}$-cycloalkyl. In a further embodiment, $R^1$ is selected from $C_3$-cycloalkyl, $C_4$-cycloalkyl, $C_5$-cycloalkyl, $C_6$-cycloalkyl and $C_7$-cycloalkyl. In a further embodiment, $R^1$ is selected from $C_{5-6}$-cycloalkyl. In a further embodiment, $R^1$ is selected from substituted $C_3$-cycloalkyl, $C_4$-cycloalkyl, $C_5$-cycloalkyl, $C_6$-cycloalkyl and $C_7$-cycloalkyl.

In an embodiment, $R^1$ is selected from phenyl and substituted phenyl.

In an embodiment, $R^2$ and $R^3$ are independently selected from $C_{1-10}$-alkyl. In a further embodiment, $R^2$ and $R^3$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^2$ and $R^3$ are independently selected from $C_{1-5}$-alkyl. In a further embodiment, $R^2$ and $R^3$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^2$ and $R^3$ are independently selected from $C_{3-7}$-cycloalkyl. In a further embodiment, $R^2$ and $R^3$ are independently selected from $C_3$-cycloalkyl, $C_4$-cycloalkyl, $C_5$-cycloalkyl, $C_6$-cycloalkyl and $C_7$-cycloalkyl. In a further embodiment, $R^2$ and $R^3$ are independently selected from $C_{5-6}$-cycloalkyl. In a further embodiment, $R^2$ and $R^3$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^2$ and $R^3$ are independently selected from phenyl and substituted phenyl.

In an embodiment, $R^4$ and $R^5$ are independently selected from $C_{1-10}$-alkyl. In a further embodiment, $R^4$ and $R^5$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^4$ and $R^5$ are independently selected from $C_{1-5}$-alkyl. In a further embodiment, $R^4$ and $R^5$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^4$ and $R^5$ are independently selected from $C_{3-7}$-cycloalkyl. In a further embodiment, $R^4$ and $R^5$ are independently selected from $C_3$-cycloalkyl, $C_4$-cycloalkyl, $C_5$-cycloalkyl, $C_6$-cycloalkyl and $C_7$-cycloalkyl. In a further embodiment, $R^4$ and $R^5$ are independently selected from $C_{5-6}$-cycloalkyl. In a further embodiment, $R^4$ and $R^5$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^4$ and $R^5$ are independently selected from phenyl and substituted phenyl.

In an embodiment, at least one of $R^4$ and $R^5$ is hydrogen.

In an embodiment, $R^4$ and $R^5$ are independently selected from a 5-membered, 6-membered, 7-membered, 8-membered or 9-membered mono or bicyclic ring system comprising an —O—B—O— bridge.

In an embodiment, $R^4$ and $R^5$ are independently selected from a substituted 5-membered, 6-membered, 7-membered, 8-membered or 9-membered mono or bicyclic ring system comprising an —O—B—O— bridge.

In an embodiment, $R^6$ is selected from $C_{1-10}$-alkyl. In a further embodiment, $R^6$ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^6$ is selected from $C_{1-5}$-alkyl. In a further embodiment, $R^6$ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^7$ and $R^8$ are independently selected from $C_{1-10}$-alkyl. In a further embodiment, $R^7$ and $R^8$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^7$ and $R^8$ are independently selected from $C_{1-5}$-alkyl. In a further embodiment, $R^7$ and $R^8$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^7$ and $R^8$ are independently selected from $C_{3-7}$-cycloalkyl. In a further embodiment, $R^7$ and $R^8$ are independently selected from $C_3$-cycloalkyl, $C_4$-cycloalkyl, $C_5$-cycloalkyl, $C_6$-cycloalkyl and $C_7$-cycloalkyl. In a further embodiment, $R^7$ and $R^8$ are independently selected from $C_{5-6}$-cycloalkyl. In a further embodiment, $R^7$ and $R^8$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^7$ and $R^8$ are independently selected from phenyl and substituted phenyl.

In an embodiment, at least one of $R^7$ and $R^8$ is hydrogen.

In an embodiment, the catalyst of Formula I is:

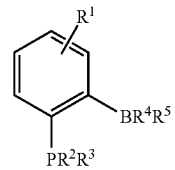

wherein:

$R^1$ is selected from hydrogen, alkyl, substituted alkyl, cycloalkyl, substituted cycloalkyl, phenyl and substituted phenyl;

$R^2$ and $R^3$ are independently selected from alkyl, substituted alkyl, cycloalkyl, substituted cycloalkyl, phenyl and substituted phenyl;

R⁴ and R⁵ are independently selected from hydrogen, alkyl, substituted alkyl, cycloalkyl, substituted cycloalkyl, phenyl, substituted phenyl, OR⁶ and NR⁷R⁸; or R⁴ and R⁵ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

R⁶ is alkyl or substituted alkyl; and

R⁷ and R⁸ are independently selected from hydrogen, alkyl, substituted alkyl, cycloalkyl, substituted cycloalkyl, phenyl and substituted phenyl.

In an embodiment, R¹ is hydrogen.

In an embodiment, R¹ is selected from $C_{1-10}$-alkyl. In a further embodiment, R¹ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, R¹ is selected from $C_{1-5}$-alkyl. In a further embodiment, R¹ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, R¹ is selected from $C_{3-7}$-cycloalkyl. In a further embodiment, R¹ is selected from $C_3$-cycloalkyl, $C_4$-cycloalkyl, $C_5$-cycloalkyl, $C_6$-cycloalkyl and $C_7$-cycloalkyl. In a further embodiment, R¹ is selected from $C_{5-6}$-cycloalkyl. In a further embodiment, R¹ is selected from substituted $C_3$-cycloalkyl, $C_4$-cycloalkyl, $C_5$-cycloalkyl, $C_6$-cycloalkyl and $C_7$-cycloalkyl.

In an embodiment, R¹ is selected from phenyl and substituted phenyl.

In an embodiment, R² and R³ are independently selected from $C_{1-10}$-alkyl. In a further embodiment, R² and R³ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, R² and R³ are independently selected from $C_{1-5}$-alkyl. In a further embodiment, R² and R³ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, R² and R³ are independently selected from $C_{3-7}$-cycloalkyl. In a further embodiment, R² and R³ are independently selected from $C_3$-cycloalkyl, $C_4$-cycloalkyl, $C_5$-cycloalkyl, $C_6$-cycloalkyl and $C_7$-cycloalkyl. In a further embodiment, R² and R³ are independently selected from $C_{5-6}$-cycloalkyl. In a further embodiment, R² and R³ are independently selected from substituted $C_3$-cycloalkyl, $C_4$-cycloalkyl, $C_5$-cycloalkyl, $C_6$-cycloalkyl and $C_7$-cycloalkyl.

In an embodiment, R² and R³ are independently selected from phenyl and substituted phenyl.

In an embodiment, R⁴ and R⁵ are independently selected from $C_{1-10}$-alkyl. In a further embodiment, R⁴ and R⁵ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, R⁴ and R⁵ are independently selected from $C_{1-5}$-alkyl. In a further embodiment, R⁴ and R⁵ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, R⁴ and R⁵ are independently selected from $C_{3-7}$-cycloalkyl. In a further embodiment, R⁴ and R⁵ are independently selected from $C_3$-cycloalkyl, $C_4$-cycloalkyl, $C_5$-cycloalkyl, $C_6$-cycloalkyl and $C_7$-cycloalkyl. In a further embodiment, R⁴ and R⁵ are independently selected from $C_{5-6}$-cycloalkyl. In a further embodiment, R⁴ and R⁵ are independently selected from substituted $C_3$-cycloalkyl, $C_4$-cycloalkyl, $C_5$-cycloalkyl, $C_6$-cycloalkyl and $C_7$-cycloalkyl.

In an embodiment, R⁴ and R⁵ are independently selected from phenyl and substituted phenyl.

In an embodiment, at least one of R⁴ and R⁵ is hydrogen.

In an embodiment, R⁴ and R⁵ are independently selected from a 5-membered, 6-membered, 7-membered, 8-membered or 9-membered mono or bicyclic ring system comprising an —O—B—O— bridge.

In an embodiment, R⁴ and R⁵ are independently selected from a substituted 5-membered, 6-membered, 7-membered, 8-membered or 9-membered mono or bicyclic ring system comprising an —O—B—O— bridge.

In an embodiment, R⁶ is selected from $C_{1-10}$-alkyl. In a further embodiment, R⁶ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, R⁶ is selected from $C_{1-5}$-alkyl. In a further embodiment, R⁶ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, R⁷ and R⁸ are independently selected from $C_{1-10}$-alkyl. In a further embodiment, R⁷ and R⁸ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, R⁷ and R⁸ are independently selected from $C_{1-5}$-alkyl. In a further embodiment, R⁷ and R⁸ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, R⁷ and R⁸ are independently selected from $C_{3-7}$-cycloalkyl. In a further embodiment, R⁷ and R⁸ are independently selected from $C_3$-cycloalkyl, $C_4$-cycloalkyl, $C_5$-cycloalkyl, $C_6$-cycloalkyl and $C_7$-cycloalkyl. In a further embodiment, R⁷ and R⁸ are independently selected from $C_{5-6}$-cycloalkyl. In a further embodiment, R⁷ and R⁸ are independently selected from substituted $C_3$-cycloalkyl, $C_4$-cycloalkyl, $C_5$-cycloalkyl, $C_6$-cycloalkyl and $C_7$-cycloalkyl.

In an embodiment, R⁷ and R⁸ are independently selected from phenyl and substituted phenyl.

In an embodiment, at least one of R⁷ and R⁸ is hydrogen.

In an embodiment, the catalyst of Formula I is:

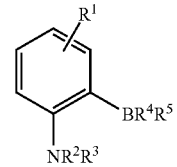

wherein:

R¹ is selected from hydrogen, alkyl, substituted alkyl, cycloalkyl, substituted cycloalkyl, phenyl and substituted phenyl;

R² and R³ are independently selected from alkyl, substituted alkyl, cycloalkyl, substituted cycloalkyl, phenyl and substituted phenyl;

R⁴ and R⁵ are independently selected from hydrogen, alkyl, substituted alkyl, cycloalkyl, substituted cycloalkyl, phenyl, substituted phenyl, OR⁶ and NR⁷R⁸; or R⁴ and R⁵ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^6$ is alkyl or substituted alkyl; and $R^7$ and $R^8$ are independently selected from hydrogen, alkyl, substituted alkyl, cycloalkyl, substituted cycloalkyl, phenyl and substituted phenyl.

In an embodiment, $R^1$ is hydrogen.

In an embodiment, $R^1$ is selected from $C_{1-10}$-alkyl. In a further embodiment, $R^1$ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^1$ is selected from $C_{1-5}$-alkyl. In a further embodiment, $R^1$ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^1$ is selected from $C_{3-7}$-cycloalkyl. In a further embodiment, $R^1$ is selected from $C_3$-cycloalkyl, $C_4$-cycloalkyl, $C_5$-cycloalkyl, $C_6$-cycloalkyl and $C_7$-cycloalkyl. In a further embodiment, $R^1$ is selected from $C_{5-6}$-cycloalkyl. In a further embodiment, $R^1$ is selected from substituted $C_3$-cycloalkyl, $C_4$-cycloalkyl, $C_5$-cycloalkyl, $C_6$-cycloalkyl and $C_7$-cycloalkyl.

In an embodiment, $R^1$ is selected from phenyl and substituted phenyl.

In an embodiment, $R^2$ and $R^3$ are independently selected from $C_{1-10}$-alkyl. In a further embodiment, $R^2$ and $R^3$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^2$ and $R^3$ are independently selected from $C_{1-5}$-alkyl. In a further embodiment, $R^2$ and $R^3$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^2$ and $R^3$ are independently selected from $C_{3-7}$-cycloalkyl. In a further embodiment, $R^2$ and $R^3$ are independently selected from $C_3$-cycloalkyl, $C_4$-cycloalkyl, $C_5$-cycloalkyl, $C_6$-cycloalkyl and $C_7$-cycloalkyl. In a further embodiment, $R^2$ and $R^3$ are independently selected from $C_{5-6}$-cycloalkyl. In a further embodiment, $R^2$ and $R^3$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^2$ and $R^3$ are independently selected from phenyl and substituted phenyl.

In an embodiment, $R^4$ and $R^5$ are independently selected from $C_{1-10}$-alkyl. In a further embodiment, $R^4$ and $R^5$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^4$ and $R^5$ are independently selected from $C_{1-5}$-alkyl. In a further embodiment, $R^4$ and $R^5$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^4$ and $R^5$ are independently selected from $C_{3-7}$-cycloalkyl. In a further embodiment, $R^4$ and $R^5$ are independently selected from $C_3$-cycloalkyl, $C_4$-cycloalkyl, $C_5$-cycloalkyl, $C_6$-cycloalkyl and $C_7$-cycloalkyl. In a further embodiment, $R^4$ and $R^5$ are independently selected from $C_{5-6}$-cycloalkyl. In a further embodiment, $R^4$ and $R^5$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^4$ and $R^5$ are independently selected from phenyl and substituted phenyl.

In an embodiment, at least one of $R^4$ and $R^5$ is hydrogen.

In an embodiment, $R^4$ and $R^5$ are independently selected from a 5-membered, 6-membered, 7-membered, 8-membered or 9-membered mono or bicyclic ring system comprising an —O—B—O— bridge.

In an embodiment, $R^4$ and $R^5$ are independently selected from a substituted 5-membered, 6-membered, 7-membered, 8-membered or 9-membered mono or bicyclic ring system comprising an —O—B—O— bridge.

In an embodiment, $R^6$ is selected from $C_{1-10}$-alkyl. In a further embodiment, $R^6$ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^6$ is selected from $C_{1-5}$-alkyl. In a further embodiment, $R^6$ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^7$ and $R^8$ are independently selected from $C_{1-10}$-alkyl. In a further embodiment, $R^7$ and $R^8$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^7$ and $R^8$ are independently selected from $C_{1-5}$-alkyl. In a further embodiment, $R^7$ and $R^8$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^7$ and $R^8$ are independently selected from $C_{3-7}$-cycloalkyl. In a further embodiment, $R^7$ and $R^8$ are independently selected from $C_3$-cycloalkyl, $C_4$-cycloalkyl, $C_5$-cycloalkyl, $C_6$-cycloalkyl and $C_7$-cycloalkyl. In a further embodiment, $R^7$ and $R^8$ are independently selected from $C_{5-6}$-cycloalkyl. In a further embodiment, $R^7$ and $R^8$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^7$ and $R^8$ are independently selected from phenyl and substituted phenyl.

In an embodiment, at least one of $R^7$ and $R^8$ is hydrogen.

In an embodiment, the catalyst of Formula I is:

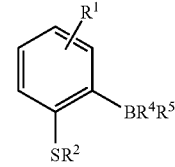

wherein:

$R^1$ is selected from hydrogen, alkyl, substituted alkyl, cycloalkyl, substituted cycloalkyl, phenyl and substituted phenyl;

$R^2$ is selected from alkyl, substituted alkyl, cycloalkyl, substituted cycloalkyl, phenyl and substituted phenyl;

$R^4$ and $R^5$ are independently selected from hydrogen, alkyl, substituted alkyl, cycloalkyl, substituted cycloalkyl, phenyl, substituted phenyl, $OR^6$ and $NR^7R^8$; or $R^4$ and $R^5$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^6$ is alkyl or substituted alkyl; and $R^7$ and $R^8$ are independently selected from hydrogen, alkyl, substituted alkyl, cycloalkyl, substituted cycloalkyl, phenyl and substituted phenyl.

In an embodiment, $R^1$ is hydrogen.

In an embodiment, $R^1$ is selected from $C_{1-10}$-alkyl. In a further embodiment, $R^1$ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^1$ is selected from $C_{1-5}$-alkyl. In a further embodiment, $R^1$ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^1$ is selected from $C_{3-7}$-cycloalkyl. In a further embodiment, $R^1$ is selected from $C_3$-cycloalkyl, $C_4$-cycloalkyl, $C_5$-cycloalkyl, $C_6$-cycloalkyl and $C_7$-cycloalkyl. In a further embodiment, $R^1$ is selected from $C_{5-6}$-cycloalkyl. In a further embodiment, $R^1$ is selected from substituted $C_3$-cycloalkyl, $C_4$-cycloalkyl, $C_5$-cycloalkyl, $C_6$-cycloalkyl and $C_7$-cycloalkyl.

In an embodiment, $R^1$ is selected from phenyl and substituted phenyl.

In an embodiment, $R^2$ is selected from $C_{1-10}$-alkyl. In a further embodiment, $R^2$ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^2$ is selected from $C_{1-5}$-alkyl. In a further embodiment, $R^2$ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^2$ is selected from $C_{3-7}$-cycloalkyl. In a further embodiment, $R^2$ is independently selected from $C_3$-cycloalkyl, $C_4$-cycloalkyl, $C_5$-cycloalkyl, $C_6$-cycloalkyl and $C_7$-cycloalkyl. In a further embodiment, $R^2$ is selected from $C_{5-6}$-cycloalkyl. In a further embodiment, $R^2$ is selected from substituted $C_3$-cycloalkyl, $C_4$-cycloalkyl, $C_5$-cycloalkyl, $C_6$-cycloalkyl and $C_7$-cycloalkyl.

In an embodiment, $R^2$ is selected from phenyl and substituted phenyl.

In an embodiment, $R^4$ and $R^5$ are independently selected from $C_{1-10}$-alkyl. In a further embodiment, $R^4$ and $R^5$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^4$ and $R^5$ are independently selected from $C_{1-5}$-alkyl. In a further embodiment, $R^4$ and $R^5$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^4$ and $R^5$ are independently selected from $C_{3-7}$-cycloalkyl. In a further embodiment, $R^4$ and $R^5$ are independently selected from $C_3$-cycloalkyl, $C_4$-cycloalkyl, $C_5$-cycloalkyl, $C_6$-cycloalkyl and $C_7$-cycloalkyl. In a further embodiment, $R^4$ and $R^5$ are independently selected from $C_{5-6}$-cycloalkyl. In a further embodiment, $R^4$ and $R^5$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^4$ and $R^5$ are independently selected from phenyl and substituted phenyl.

In an embodiment, at least one of $R^4$ and $R^5$ is hydrogen.

In an embodiment, $R^4$ and $R^5$ are independently selected from a 5-membered, 6-membered, 7-membered, 8-membered or 9-membered mono or bicyclic ring system comprising an —O—B—O— bridge.

In an embodiment, $R^4$ and $R^5$ are independently selected from a substituted 5-membered, 6-membered, 7-membered, 8-membered or 9-membered mono or bicyclic ring system comprising an —O—B—O— bridge.

In an embodiment, $R^6$ is selected from $C_{1-10}$-alkyl. In a further embodiment, $R^6$ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^6$ is selected from $C_{1-5}$-alkyl. In a further embodiment, $R^6$ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^7$ and $R^8$ are independently selected from $C_{1-10}$-alkyl. In a further embodiment, $R^7$ and $R^8$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^7$ and $R^8$ are independently selected from $C_{1-5}$-alkyl. In a further embodiment, $R^7$ and $R^8$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^7$ and $R^8$ are independently selected from $C_{3-7}$-cycloalkyl. In a further embodiment, $R^7$ and $R^8$ are independently selected from $C_3$-cycloalkyl, $C_4$-cycloalkyl, $C_5$-cycloalkyl, $C_6$-cycloalkyl and $C_7$-cycloalkyl. In a further embodiment, $R^7$ and $R^8$ are independently selected from $C_{5-6}$-cycloalkyl. In a further embodiment, $R^7$ and $R^8$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^7$ and $R^8$ are independently selected from phenyl and substituted phenyl.

In an embodiment, at least one of $R^7$ and $R^8$ is hydrogen.

In an embodiment, $PR^2R^3$ is selected from:

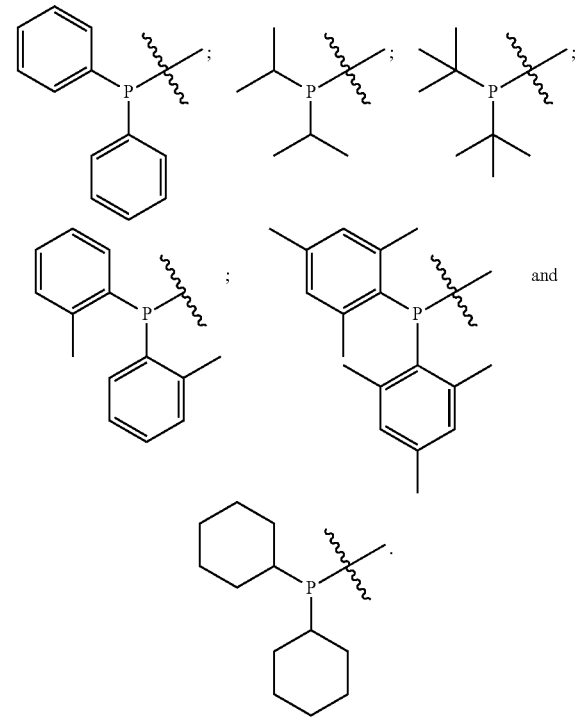

In an embodiment, $NR^2R^3$ is selected from:

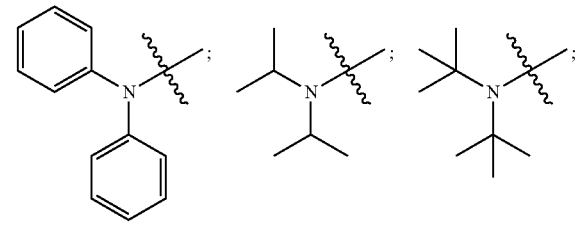

-continued

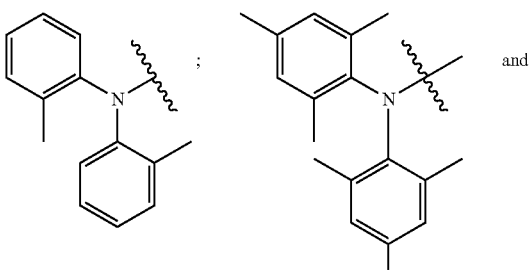

In an embodiment, SR² is selected from:

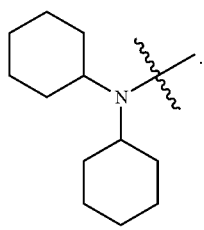

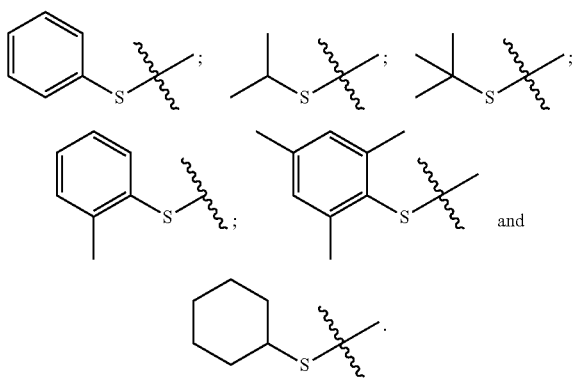

In an embodiment, BR⁴R⁵ is selected from:

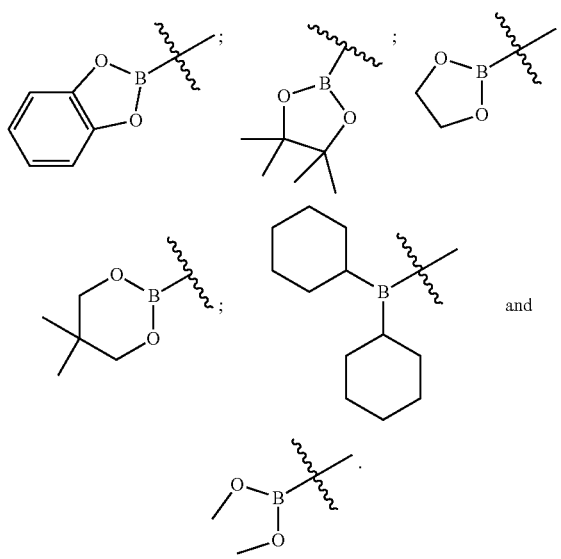

In an embodiment, the catalyst of Formula I is:

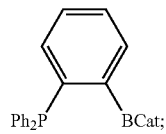

wherein Cat is a catechol group.

In an embodiment, the present disclosure includes a catalyst of Formula II:

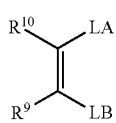

Formula II wherein:
LB is a Lewis base;
LA is a Lewis acid; and
$R^9$ and $R^{10}$ are independently selected from alkyl, substituted alkyl, cycloalkyl, substituted cycloalkyl, phenyl and substituted phenyl.

In an embodiment, $R^9$ and $R^{10}$ are independently selected from $C_{1-10}$-alkyl. In a further embodiment, $R^9$ and $R^{10}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^9$ and $R^{10}$ are independently selected from $C_{1-5}$-alkyl. In a further embodiment, $R^9$ and $R^{10}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^9$ and $R^{10}$ are independently selected from $C_{3-7}$-cycloalkyl. In a further embodiment, $R^9$ and $R^{10}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^9$ and $R^{10}$ are independently selected from $C_{5-6}$-cycloalkyl. In a further embodiment, $R^9$ and $R^{10}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^9$ and $R^{10}$ are independently selected from phenyl and substituted phenyl.

In an embodiment, the catalyst of Formula II is:

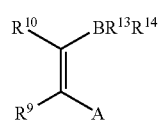

wherein:
A is selected from is selected from $PR^{11}R^{12}$, $NR^{11}R^{12}$ and $SR^{11}$;
$R^9$, $R^{10}$, $R^{11}$ and $R^{12}$ are independently selected from alkyl, substituted alkyl, cycloalkyl, substituted cycloalkyl, phenyl and substituted phenyl;
$R^{13}$ and $R^{14}$ are independently selected from hydrogen, alkyl, substituted alkyl, cycloalkyl, substituted cycloalkyl, phenyl, substituted phenyl, $OR^{15}$ and $NR^{16}R^{17}$; or
$R^{13}$ and $R^{14}$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^{15}$ is alkyl or substituted alkyl; and $R^{16}$ and $R^{17}$ are independently selected from hydrogen, alkyl, substituted alkyl, cycloalkyl, substituted cycloalkyl, phenyl and substituted phenyl.

In an embodiment, $R^9$, $R^{10}$, $R^{11}$ and $R^{12}$ are independently selected from $C_{1-10}$-alkyl. In a further embodiment, $R^9$, $R^{10}$, $R^{11}$ and $R^{12}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^9$, $R^{10}$, $R^{11}$ and $R^{12}$ are independently selected from $C_{1-5}$-alkyl. In a further embodiment, $R^9$, $R^{10}$, $R^{11}$ and $R^{12}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^9$, $R^{10}$, $R^{11}$ and $R^{12}$ are independently selected from $C_{3-7}$-cycloalkyl. In a further embodiment, $R^9$, $R^{10}$, $R^{11}$ and $R^{12}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^9$, $R^{10}$, $R^{11}$ and $R^{12}$ are independently selected from $C_{5-6}$-cycloalkyl. In a further embodiment, $R^9$, $R^{10}$, $R^{11}$ and $R^{12}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^9$, $R^{10}$, $R^{11}$ and $R^{12}$ are independently selected from phenyl and substituted phenyl.

In an embodiment, $R^{13}$ and $R^{14}$ are independently selected from $C_{1-10}$-alkyl. In a further embodiment, $R^{13}$ and $R^{14}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{13}$ and $R^{14}$ are independently selected from $C_{1-5}$-alkyl. In a further embodiment, $R^{13}$ and $R^{14}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{13}$ and $R^{14}$ are independently selected from $C_{3-7}$-cycloalkyl. In a further embodiment, $R^{13}$ and $R^{14}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^{13}$ and $R^{14}$ are independently selected from $C_{5-6}$-cycloalkyl. In a further embodiment, $R^{13}$ and $R^{14}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^{13}$ and $R^{14}$ are independently selected from phenyl and substituted phenyl.

In an embodiment, at least one of $R^{13}$ and $R^{14}$ is hydrogen.

In an embodiment, $R^{13}$ and $R^{14}$ are independently selected from a 5-membered, 6-membered, 7-membered, 8-membered or 9-membered mono or bicyclic ring system comprising an —O—B—O— bridge.

In an embodiment, $R^{13}$ and $R^{14}$ are independently selected from a substituted 5-membered, 6-membered, 7-membered, 8-membered or 9-membered mono or bicyclic ring system comprising an —O—B—O— bridge.

In an embodiment, $R^{15}$ is selected from $C_{1-10}$-alkyl. In a further embodiment, $R^{15}$ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{15}$ is selected from $C_{1-5}$-alkyl. In a further embodiment, $R^{15}$ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{16}$ and $R^{17}$ are independently selected from $C_{1-10}$-alkyl. In a further embodiment, $R^{16}$ and $R^{17}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{16}$ and $R^{17}$ are independently selected from $C_{1-5}$-alkyl. In a further embodiment, $R^{16}$ and $R^{17}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{16}$ and $R^{17}$ are independently selected from $C_{3-7}$-cycloalkyl. In a further embodiment, $R^{16}$ and $R^{17}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^{16}$ and $R^{17}$ are independently selected from $C_{5-6}$-cycloalkyl. In a further embodiment, $R^{16}$ and $R^{17}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^{16}$ and $R^{17}$ are independently selected from phenyl and substituted phenyl.

In an embodiment, at least one of $R^{16}$ and $R^{17}$ is hydrogen.

In an embodiment, the catalyst of Formula II is:

$$\begin{array}{c} R^{10} \diagdown \quad \diagup BR^{13}R^{14} \\ \Big\| \\ R^9 \diagup \quad \diagdown PR^{11}R^{12} \end{array}$$

wherein:

$R^9$, $R^{10}$, $R^{11}$ and $R^{12}$ are independently selected from alkyl, substituted alkyl, cycloalkyl, substituted cycloalkyl, phenyl and substituted phenyl;

$R^{13}$ and $R^{14}$ are independently selected from hydrogen, alkyl, substituted alkyl, cycloalkyl, substituted cycloalkyl, phenyl, substituted phenyl, $OR^{15}$ and $NR^{16}R^{17}$; or $R^{13}$ and $R^{14}$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^{15}$ is alkyl or substituted alkyl; and $R^{16}$ and $R^{17}$ are independently selected from hydrogen, alkyl, substituted alkyl, cycloalkyl, substituted cycloalkyl, phenyl and substituted phenyl.

In an embodiment, $R^9$, $R^{10}$, $R^{11}$ and $R^{12}$ are independently selected from $C_{1-10}$-alkyl. In a further embodiment, $R^9$, $R^{10}$, $R^{11}$ and $R^{12}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^9$, $R^{10}$, $R^{11}$ and $R^{12}$ are independently selected from $C_{1-5}$-alkyl. In a further embodiment, $R^9$, $R^{10}$, $R^{11}$ and $R^{12}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^9$, $R^{10}$, $R^{11}$ and $R^{12}$ are independently selected from $C_{3-7}$-cycloalkyl. In a further embodiment, $R^9$, $R^{10}$, $R^{11}$ and $R^{12}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^9$, $R^{10}$, $R^{11}$ and $R^{12}$ are independently selected from $C_{5-6}$-cycloalkyl. In a further embodiment, $R^9$, $R^{10}$, $R^{11}$ and $R^{12}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^9$, $R^{10}$, $R^{11}$ and $R^{12}$ are independently selected from phenyl and substituted phenyl.

In an embodiment, $R^{13}$ and $R^{14}$ are independently selected from $C_{1-10}$-alkyl. In a further embodiment, $R^{13}$ and $R^{14}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{13}$ and $R^{14}$ are independently selected from $C_{1-5}$-alkyl. In a further embodiment, $R^{13}$ and $R^{14}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{13}$ and $R^{14}$ are independently selected from $C_{3-7}$-cycloalkyl. In a further embodiment, $R^{13}$ and $R^{14}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^{13}$ and $R^{14}$ are independently selected from $C_{5-6}$-cycloalkyl. In a further embodiment, $R^{13}$ and $R^{14}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^{13}$ and $R^{14}$ are independently selected from phenyl and substituted phenyl.

In an embodiment, at least one of $R^{13}$ and $R^{14}$ is hydrogen.

In an embodiment, $R^{13}$ and $R^{14}$ are independently selected from a 5-membered, 6-membered, 7-membered, 8-membered or 9-membered mono or bicyclic ring system comprising an —O—B—O— bridge.

In an embodiment, $R^{13}$ and $R^{14}$ are independently selected from a substituted 5-membered, 6-membered, 7-membered, 8-membered or 9-membered mono or bicyclic ring system comprising an —O—B—O— bridge.

In an embodiment, $R^{15}$ is selected from $C_{1-10}$-alkyl. In a further embodiment, $R^{15}$ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{15}$ is selected from $C_{1-5}$-alkyl. In a further embodiment, $R^{15}$ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{16}$ and $R^{17}$ are independently selected from $C_{1-10}$-alkyl. In a further embodiment, $R^{16}$ and $R^{17}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{16}$ and $R^{17}$ are independently selected from $C_{1-5}$-alkyl. In a further embodiment, $R^{16}$ and $R^{17}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{16}$ and $R^{17}$ are independently selected from $C_{3-7}$-cycloalkyl. In a further embodiment, $R^{16}$ and $R^{17}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^{16}$ and $R^{17}$ are independently selected from $C_{5-6}$-cycloalkyl. In a further embodiment, $R^{16}$ and $R^{17}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^{16}$ and $R^{17}$ are independently selected from phenyl and substituted phenyl.

In an embodiment, at least one of $R^{16}$ and $R^{17}$ is hydrogen.

In an embodiment, the catalyst of Formula II is:

$$R^{10}\diagdown\diagup BR^{13}R^{14}$$
$$R^9\diagup\diagdown NR^{11}R^{12}$$

wherein:

$R^9$, $R^{10}$, $R^{11}$ and $R^{12}$ are independently selected from alkyl, substituted alkyl, cycloalkyl, substituted cycloalkyl, phenyl and substituted phenyl;

$R^{13}$ and $R^{14}$ are independently selected from hydrogen, alkyl, substituted alkyl, cycloalkyl, substituted cycloalkyl, phenyl, substituted phenyl, $OR^{15}$ and $NR^{16}R^{17}$; or $R^{13}$ and $R^{14}$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^{15}$ is alkyl or substituted alkyl; and $R^{16}$ and $R^{17}$ are independently selected from hydrogen, alkyl, substituted alkyl, cycloalkyl, substituted cycloalkyl, phenyl and substituted phenyl.

In an embodiment, $R^9$, $R^{10}$, $R^{11}$ and $R^{12}$ are independently selected from $C_{1-10}$-alkyl. In a further embodiment, $R^9$, $R^{10}$, $R^{11}$ and $R^{12}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^9$, $R^{10}$, $R^{11}$ and $R^{12}$ are independently selected from $C_{1-5}$-alkyl. In a further embodiment, $R^9$, $R^{10}$, $R^{11}$ and $R^{12}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^9$, $R^{10}$, $R^{11}$ and $R^{12}$ are independently selected from $C_{3-7}$-cycloalkyl. In a further embodiment, $R^9$, $R^{10}$, $R^{11}$ and $R^{12}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^9$, $R^{10}$, $R^{11}$ and $R^{12}$ are independently selected from $C_{5-6}$-cycloalkyl. In a further embodiment, $R^9$, $R^{10}$, $R^{11}$ and $R^{12}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^9$, $R^{10}$, $R^{11}$ and $R^{12}$ are independently selected from phenyl and substituted phenyl.

In an embodiment, $R^{13}$ and $R^{14}$ are independently selected from $C_{1-10}$-alkyl. In a further embodiment, $R^{13}$ and $R^{14}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{13}$ and $R^{14}$ are independently selected from $C_{1-5}$-alkyl. In a further embodiment, $R^{13}$ and $R^{14}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{13}$ and $R^{14}$ are independently selected from $C_{3-7}$-cycloalkyl. In a further embodiment, $R^{13}$ and $R^{14}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^{13}$ and $R^{14}$ are independently selected from $C_{5-6}$-cycloalkyl. In a further embodiment, $R^{13}$ and $R^{14}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^{13}$ and $R^{14}$ are independently selected from phenyl and substituted phenyl.

In an embodiment, at least one of $R^{13}$ and $R^{14}$ is hydrogen.

In an embodiment, $R^{13}$ and $R^{14}$ are independently selected from a 5-membered, 6-membered, 7-membered, 8-membered or 9-membered mono or bicyclic ring system comprising an —O—B—O— bridge.

In an embodiment, $R^{13}$ and $R^{14}$ are independently selected from a substituted 5-membered, 6-membered, 7-membered, 8-membered or 9-membered mono or bicyclic ring system comprising an —O—B—O— bridge.

In an embodiment, $R^{15}$ is selected from $C_{1-10}$-alkyl. In a further embodiment, $R^{15}$ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{15}$ is selected from $C_{1-5}$-alkyl. In a further embodiment, $R^{15}$ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{16}$ and $R^{17}$ are independently selected from $C_{1-10}$-alkyl. In a further embodiment, $R^{16}$ and $R^{17}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{16}$ and $R^{17}$ are independently selected from $C_{1-5}$-alkyl. In a further embodiment, $R^{16}$ and $R^{17}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{16}$ and $R^{17}$ are independently selected from $C_{3-7}$-cycloalkyl. In a further embodiment, $R^{16}$ and $R^{17}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^{16}$ and $R^{17}$ are independently selected from $C_{5-6}$-cycloalkyl. In a further embodiment, $R^{16}$ and $R^{17}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^{16}$ and $R^{17}$ are independently selected from phenyl and substituted phenyl.

In an embodiment, at least one of $R^{16}$ and $R^{17}$ is hydrogen.

In an embodiment, the catalyst of Formula II is:

$$\underset{R^9}{\overset{R^{10}}{\diagup}}C=C\underset{SR^{11}}{\overset{BR^{13}R^{14}}{\diagup}}$$

wherein:

$R^9$, $R^{10}$ and $R^{11}$ are independently selected from alkyl, substituted alkyl, cycloalkyl, substituted cycloalkyl, phenyl and substituted phenyl;

$R^{13}$ and $R^{14}$ are independently selected from hydrogen, alkyl, substituted alkyl, cycloalkyl, substituted cycloalkyl, phenyl, substituted phenyl, $OR^{15}$ and $NR^{16}R^{17}$; or $R^{13}$ and $R^{14}$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^{15}$ is alkyl or substituted alkyl; and $R^{16}$ and $R^{17}$ are independently selected from hydrogen, alkyl, substituted alkyl, cycloalkyl, substituted cycloalkyl, phenyl and substituted phenyl.

In an embodiment, $R^9$, $R^{10}$ and $R^{11}$ are independently selected from $C_{1-10}$-alkyl. In a further embodiment, $R^9$, $R^{10}$ and $R^{11}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^9$, $R^{10}$ and $R^{11}$ are independently selected from $C_{1-5}$-alkyl. In a further embodiment, $R^9$, $R^{10}$ and $R^{11}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^9$, $R^{10}$ and $R^{11}$ are independently selected from $C_{3-7}$-cycloalkyl. In a further embodiment, $R^9$, $R^{10}$ and $R^{11}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^9$, $R^{10}$ and $R^{11}$ are independently selected from $C_{5-6}$-cycloalkyl. In a further embodiment, $R^9$, $R^{10}$ and $R^{11}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^9$, $R^{10}$ and $R^{11}$ are independently selected from phenyl and substituted phenyl.

In an embodiment, $R^{13}$ and $R^{14}$ are independently selected from $C_{1-10}$-alkyl. In a further embodiment, $R^{13}$ and $R^{14}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{13}$ and $R^{14}$ are independently selected from $C_{1-5}$-alkyl. In a further embodiment, $R^{13}$ and $R^{14}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{13}$ and $R^{14}$ are independently selected from $C_{3-7}$-cycloalkyl. In a further embodiment, $R^{13}$ and $R^{14}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^{13}$ and $R^{14}$ are independently selected from $C_{5-6}$-cycloalkyl. In a further embodiment, $R^{13}$ and $R^{14}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^{13}$ and $R^{14}$ are independently selected from phenyl and substituted phenyl.

In an embodiment, at least one of $R^{13}$ and $R^{14}$ is hydrogen.

In an embodiment, $R^{13}$ and $R^{14}$ are independently selected from a 5-membered, 6-membered, 7-membered, 8-membered or 9-membered mono or bicyclic ring system comprising an —O—B—O— bridge.

In an embodiment, $R^{13}$ and $R^{14}$ are independently selected from a substituted 5-membered, 6-membered, 7-membered, 8-membered or 9-membered mono or bicyclic ring system comprising an —O—B—O— bridge.

In an embodiment, $R^{15}$ is selected from $C_{1-10}$-alkyl. In a further embodiment, $R^{15}$ is selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{15}$ is selected from $C_{1-5}$-alkyl. In a further embodiment, $R^{15}$ is selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{16}$ and $R^{17}$ are independently selected from $C_{1-10}$-alkyl. In a further embodiment, $R^{16}$ and $R^{17}$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, and $C_{10}$-alkyl. In a further embodiment, $R^{16}$ and $R^{17}$ are independently selected from $C_{1-5}$-alkyl. In a further embodiment, $R^{16}$ and $R^{17}$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

In an embodiment, $R^{16}$ and $R^{17}$ are independently selected from $C_{3-7}$-cycloalkyl. In a further embodiment, $R^{16}$ and $R^{17}$ are independently selected from $C_3$-cycloalkyl, $C_4$-cycloalkyl, $C_5$-cycloalkyl, $C_6$-cycloalkyl and $C_7$-cycloalkyl. In a further embodiment, $R^{16}$ and $R^{17}$ are independently selected from $C_{5-6}$-cycloalkyl. In a further embodiment, $R^{16}$ and $R^{17}$ are independently selected from substituted $C_3$-cycloalkyl, $C_4$-cycloalkyl, $C_5$-cycloalkyl, $C_6$-cycloalkyl and $C_7$-cycloalkyl.

In an embodiment, $R^{16}$ and $R^{17}$ are independently selected from phenyl and substituted phenyl.

In an embodiment, at least one of $R^{16}$ and $R^{17}$ is hydrogen.

In an embodiment, $PR^{11}R^{12}$ is selected from:

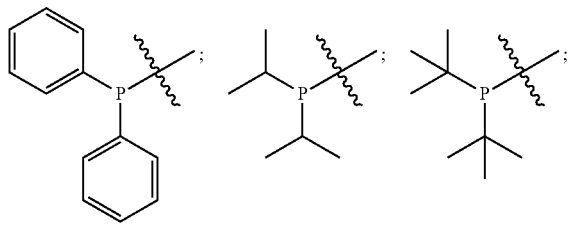

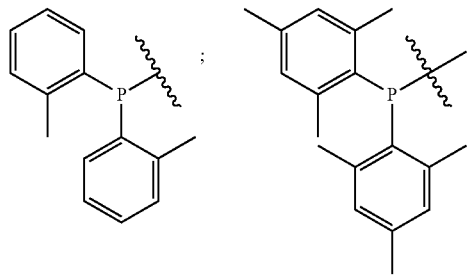

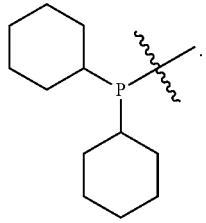

In an embodiment, $NR^{11}R^{12}$ is selected from:

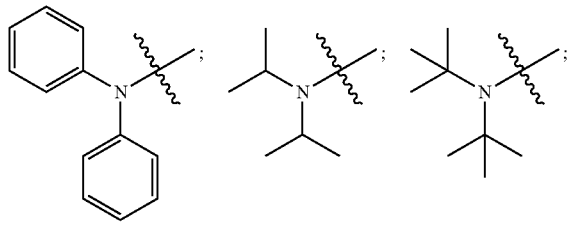

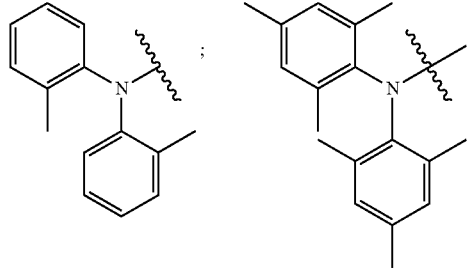

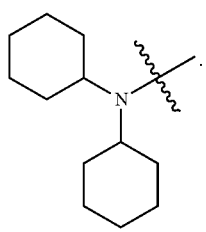

In an embodiment, $SR^{11}$ is selected from:

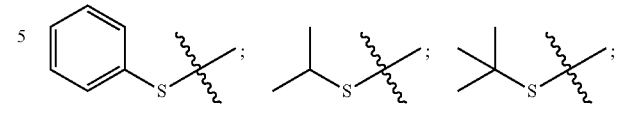

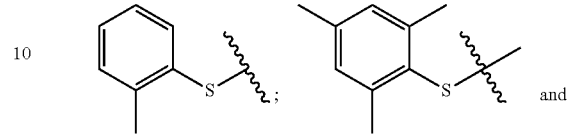

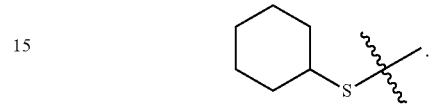

In an embodiment, $BR^{13}R^{14}$ is selected from:

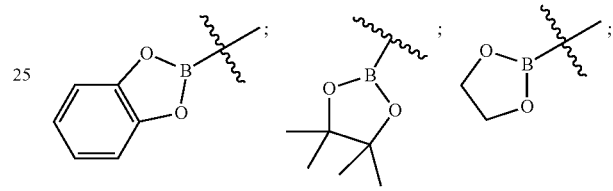

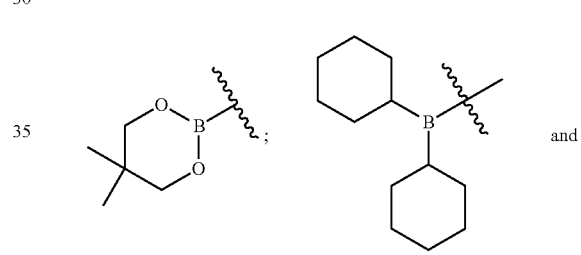

In another embodiment, the present disclosure relates to a catalytic composition for the production of methanol from carbon dioxide, the composition comprising at least one catalyst selected from Formula I and Formula II. In a further embodiment of the disclosure, the catalysts of Formula I and Formula II convert carbon dioxide into a methoxyborane species that is subsequently hydrolyzed to generate methanol. In yet another embodiment, the present disclosure relates to a catalytic composition for the production of methanol from carbon dioxide, the composition comprising at least one catalyst selected from Formula I and Formula II and a hydrogen source. In yet a further embodiment, the hydrogen source comprises a hydroborane. Non-limiting examples of hydroboranes include HBCat, HBPin, 9-BBN and $BH_3$—$SMe_2$.

In an embodiment, the present disclosure includes a process for the production of methanol from $CO_2$, the process comprising:

combining a catalyst having the Formula:

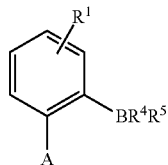

wherein:
A is selected from $PR^2R^3$, $NR^2R^3$ and $SR^2$;
$R^1$ is selected from hydrogen, alkyl, substituted alkyl, cycloalkyl, substituted cycloalkyl, phenyl and substituted phenyl;
$R^2$ and $R^3$ are independently selected from alkyl, substituted alkyl, cycloalkyl, substituted cycloalkyl, phenyl and substituted phenyl;
$R^4$ and $R^5$ are independently selected from hydrogen, alkyl, substituted alkyl, cycloalkyl, substituted cycloalkyl, phenyl, substituted phenyl, $OR^5$ and $NR^7R^8$; or
$R^4$ and $R^5$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;
$R^6$ is alkyl or substituted alkyl; and
$R^7$ and $R^8$ are independently selected from hydrogen, alkyl, substituted alkyl, cycloalkyl, substituted cycloalkyl, phenyl and substituted phenyl; and
a hydrogen source to produce a mixture;
exposing the mixture to $CO_2$ under conditions to convert the $CO_2$ into methoxyboranes; and
hydrolyzing the methoxyboranes to produce methanol.

In an embodiment, the present disclosure includes a process for the production of methanol from $CO_2$, the process comprising:
combining a catalyst having the Formula:

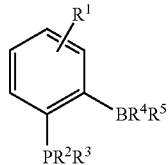

wherein:
$R^1$ is selected from hydrogen, alkyl, substituted alkyl, cycloalkyl, substituted cycloalkyl, phenyl and substituted phenyl;
$R^2$ and $R^3$ are independently selected from alkyl, substituted alkyl, cycloalkyl, substituted cycloalkyl, phenyl and substituted phenyl;
$R^4$ and $R^5$ are independently selected from hydrogen, alkyl, substituted alkyl, cycloalkyl, substituted cycloalkyl, phenyl, substituted phenyl, $OR^6$ and $NR^7R^8$; or
$R^4$ and $R^5$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;
$R^6$ is alkyl or substituted alkyl; and
$R^7$ and $R^8$ are independently selected from hydrogen, alkyl, substituted alkyl, cycloalkyl, substituted cycloalkyl, phenyl and substituted phenyl; and
a hydrogen source to produce a mixture;
exposing the mixture to $CO_2$ under conditions to convert the $CO_2$ into methoxyboranes; and
hydrolyzing the methoxyboranes to produce methanol.

In an embodiment, the present disclosure includes a process for the production of methanol from $CO_2$, the process comprising:
combining a catalyst having the Formula:

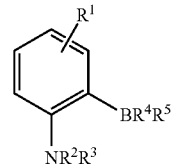

wherein:
$R^1$ is selected from hydrogen, alkyl, substituted alkyl, cycloalkyl, substituted cycloalkyl, phenyl and substituted phenyl;
$R^2$ and $R^3$ are independently selected from alkyl, substituted alkyl, cycloalkyl, substituted cycloalkyl, phenyl and substituted phenyl;
$R^4$ and $R^5$ are independently selected from hydrogen, alkyl, substituted alkyl, cycloalkyl, substituted cycloalkyl, phenyl, substituted phenyl, $OR^6$ and $NR^7R^8$; or
$R^4$ and $R^5$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;
$R^6$ is alkyl or substituted alkyl; and
$R^7$ and $R^8$ are independently selected from hydrogen, alkyl, substituted alkyl, cycloalkyl, substituted cycloalkyl, phenyl and substituted phenyl; and
a hydrogen source to produce a mixture;
exposing the mixture to $CO_2$ under conditions to convert the $CO_2$ into methoxyboranes; and
hydrolyzing the methoxyboranes to produce methanol.

In an embodiment, the present disclosure includes a process for the production of methanol from $CO_2$, the process comprising:
combining a catalyst having the Formula:

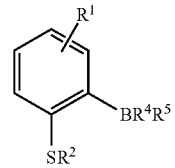

wherein:
$R^1$ is selected from hydrogen, alkyl, substituted alkyl, cycloalkyl, substituted cycloalkyl, phenyl and substituted phenyl;
$R^2$ is selected from alkyl, substituted alkyl, cycloalkyl, substituted cycloalkyl, phenyl and substituted phenyl;
$R^4$ and $R^5$ are independently selected from hydrogen, alkyl, substituted alkyl, cycloalkyl, substituted cycloalkyl, phenyl, substituted phenyl, $OR^6$ and $NR^7R^8$; or
$R^4$ and $R^5$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^6$ is alkyl or substituted alkyl; and $R^7$ and $R^8$ are independently selected from hydrogen, alkyl, substituted alkyl, cycloalkyl, substituted cycloalkyl, phenyl and substituted phenyl; and a hydrogen source to produce a mixture;

exposing the mixture to $CO_2$ under conditions to convert the $CO_2$ into methoxyboranes; and hydrolyzing the methoxyboranes to produce methanol.

In an embodiment, $PR^2R^3$ is selected from:

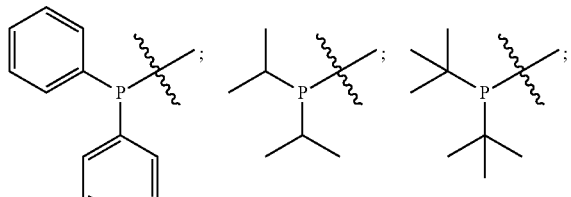

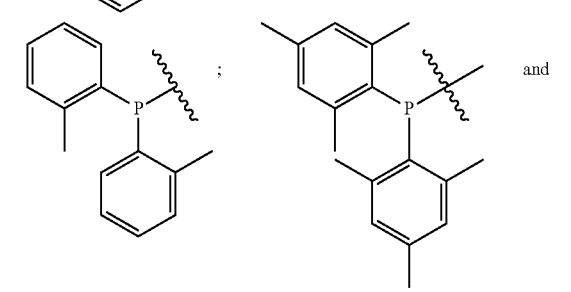

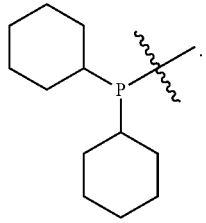

In an embodiment, $NR^2R^3$ is selected from:

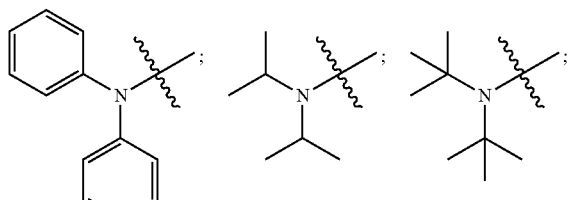

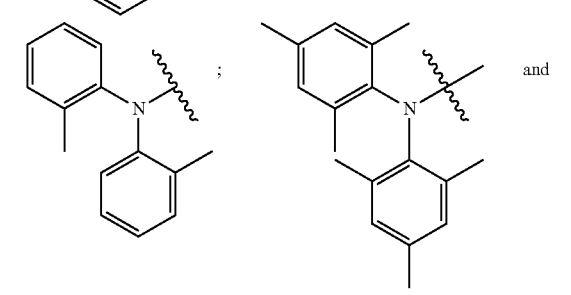

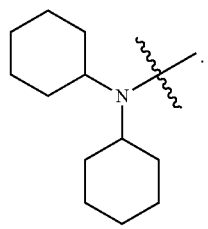

In an embodiment, $SR^2$ is selected from:

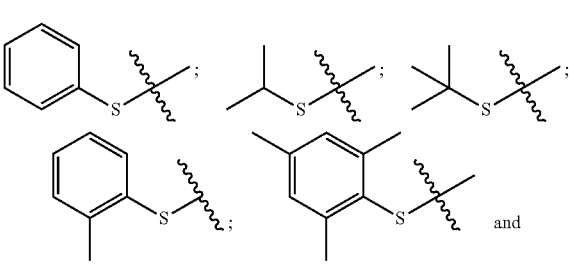

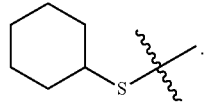

In an embodiment, $BR^4R^5$ is selected from:

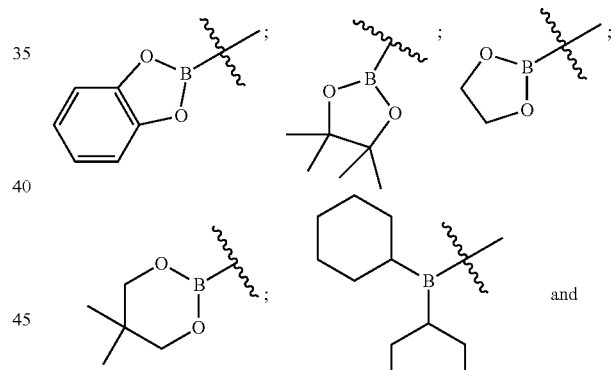

In an embodiment, the present disclosure includes a process for the production of methanol from $CO_2$, the process comprising:

combining a catalyst having the Formula:

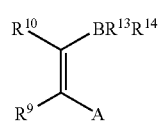

wherein:

A is selected from $PR^{11}R^{12}$, $NR^{11}R^{12}$ and $SR^{11}$;

$R^9$, $R^{10}$, $R^{11}$ and $R^{12}$ are independently selected from alkyl, substituted alkyl, cycloalkyl, substituted cycloalkyl, phenyl and substituted phenyl;

$R^{13}$ and $R^{14}$ are independently selected from hydrogen, alkyl, substituted alkyl, cycloalkyl, substituted cycloalkyl, phenyl, substituted phenyl, $OR^{15}$ and $NR^{16}R^{17}$; or $R^{13}$ and $R^{14}$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^{15}$ is alkyl or substituted alkyl; and $R^{16}$ and $R^{17}$ are independently selected from hydrogen, alkyl, substituted alkyl, cycloalkyl, substituted cycloalkyl, phenyl and substituted phenyl; and a hydrogen source to produce a mixture;

exposing the mixture to $CO_2$ under conditions to convert the $CO_2$ into methoxyboranes; and hydrolyzing the methoxyboranes to produce methanol.

In an embodiment, the present disclosure includes a process for the production of methanol from $CO_2$, the process comprising:

combining a catalyst having the Formula:

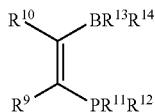

wherein:

$R^9$, $R^{10}$, $R^{11}$ and $R^{12}$ are independently selected from alkyl, substituted alkyl, cycloalkyl, substituted cycloalkyl, phenyl and substituted phenyl;

$R^{13}$ and $R^{14}$ are independently selected from hydrogen, alkyl, substituted alkyl, cycloalkyl, substituted cycloalkyl, phenyl, substituted phenyl, $OR^{15}$ and $NR^{16}R^{17}$; or $R^{13}$ and $R^{14}$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^{15}$ is alkyl or substituted alkyl; and $R^{15}$ and $R^{17}$ are independently selected from hydrogen, alkyl, substituted alkyl, cycloalkyl, substituted cycloalkyl, phenyl and substituted phenyl; and a hydrogen source to produce a mixture;

exposing the mixture to $CO_2$ under conditions to convert the $CO_2$ into methoxyboranes; and hydrolyzing the methoxyboranes to produce methanol.

In an embodiment, the present disclosure includes a process for the production of methanol from $CO_2$, the process comprising:

combining a catalyst having the Formula:

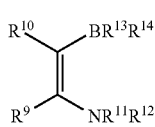

wherein:

$R^9$, $R^{19}$, $R^{11}$ and $R^{12}$ are independently selected from alkyl, substituted alkyl, cycloalkyl, substituted cycloalkyl, phenyl and substituted phenyl;

$R^{13}$ and $R^{14}$ are independently selected from hydrogen, alkyl, substituted alkyl, cycloalkyl, substituted cycloalkyl, phenyl, substituted phenyl, $OR^{15}$ and $NR^{16}R^{17}$; or $R^{13}$ and $R^{14}$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^{15}$ is alkyl or substituted alkyl; and $R^{16}$ and $R^{17}$ are independently selected from hydrogen, alkyl, substituted alkyl, cycloalkyl, substituted cycloalkyl, phenyl and substituted phenyl; and a hydrogen source to produce a mixture;

exposing the mixture to $CO_2$ under conditions to convert the $CO_2$ into methoxyboranes; and hydrolyzing the methoxyboranes to produce methanol.

In an embodiment, the present disclosure includes a process for the production of methanol from $CO_2$, the process comprising:

combining a catalyst having the Formula:

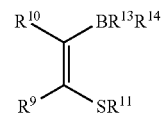

wherein:

$R^9$, $R^{10}$ and $R^{11}$ are independently selected from alkyl, substituted alkyl, cycloalkyl, substituted cycloalkyl, phenyl and substituted phenyl;

$R^{13}$ and $R^{14}$ are independently selected from hydrogen, alkyl, substituted alkyl, cycloalkyl, substituted cycloalkyl, phenyl, substituted phenyl, $OR^{15}$ and $NR^{16}R^{17}$; or $R^{13}$ and $R^{14}$ are connected together by an —O—B—O— bridge to form, together with the carbon atoms to which they are attached, a 5-, 6-, 7-, 8 or 9-membered mono or bicyclic ring system or a substituted 5-, 6-, 7-, 8 or 9-membered mono or bicyclic ring system;

$R^{15}$ is alkyl or substituted alkyl; and $R^{16}$ and $R^{17}$ are independently selected from hydrogen, alkyl, substituted alkyl, cycloalkyl, substituted cycloalkyl, phenyl and substituted phenyl; and a hydrogen source to produce a mixture;

exposing the mixture to $CO_2$ under conditions to convert the $CO_2$ into methoxyboranes; and hydrolyzing the methoxyboranes to produce methanol.

In an embodiment, $PR^{11}R^{12}$ is selected from:

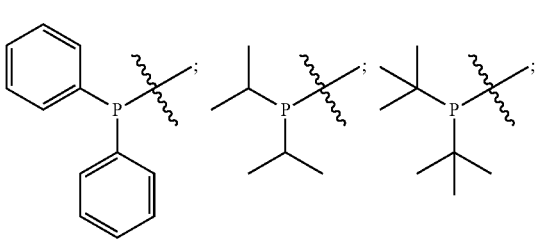

-continued

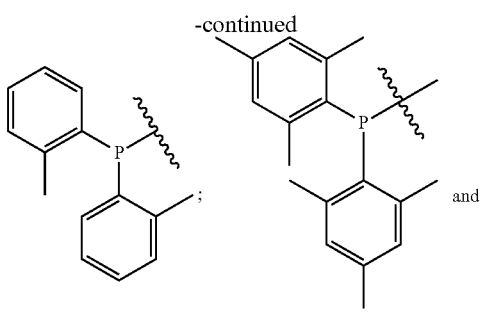
and

In an embodiment, $NR^{11}R^{12}$ is selected from:

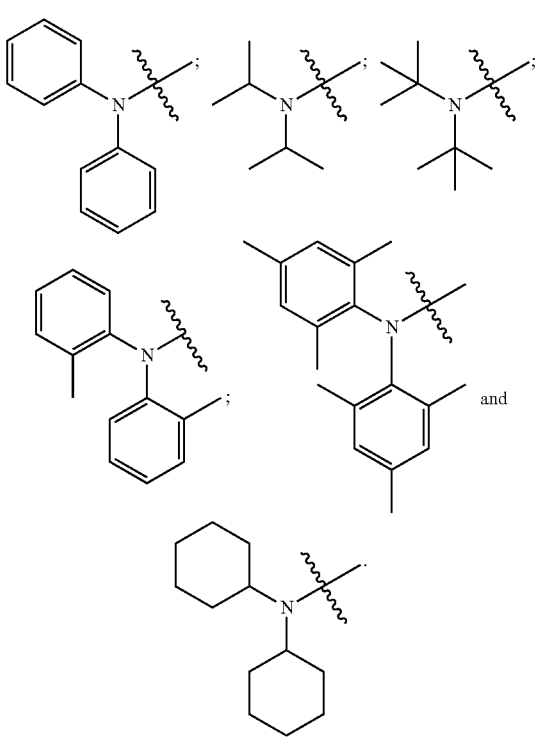

In an embodiment, $SR^{11}$ is selected from:

-continued

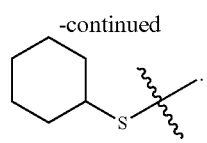

In an embodiment, $BR^{13}R^{14}$ is selected from:

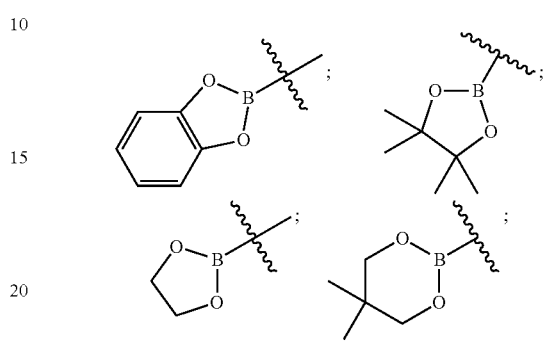

and

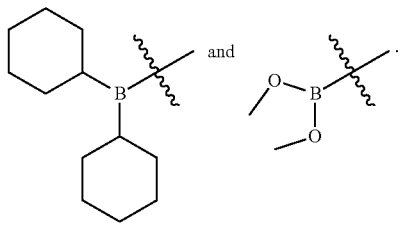

In an embodiment of the present disclosure, the catalysts of Formula I are converted in situ to a structure of Formula:

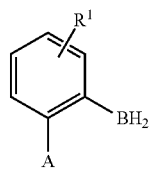

wherein:
A is selected from $PR^2R^3$, $NR^2R^3$ and $SR^2$;
$R^1$ is selected from hydrogen, alkyl, substituted alkyl, cycloalkyl, substituted cycloalkyl, phenyl and substituted phenyl; and
$R^1$ and $R^2$ are independently selected from alkyl, substituted alkyl, cycloalkyl, substituted cycloalkyl, phenyl and substituted phenyl.

In an embodiment of the present disclosure, the catalysts of Formula II are converted in situ to a structure of Formula:

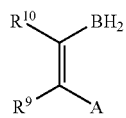

wherein:
A is selected from is selected from $PR^{11}R^{12}$, $NR^{11}R^{12}$ and $SR^{11}$;
$R^9$, $R^{10}$, $R^{11}$ and $R^{12}$ are independently selected from alkyl, substituted alkyl, cycloalkyl, substituted cycloalkyl, phenyl and substituted phenyl.

The foregoing and other advantages and features of the present disclosure will become more apparent upon reading of the following non-restrictive description of illustrative embodiments thereof, given by way of example only with reference to the accompanying drawings/figures.

BRIEF DESCRIPTION OF THE DRAWINGS/FIGURES

In the appended drawings/figures:

FIG. 1 is an ORTEP drawing of derivative 2 with anisotropic atomic displacement ellipsoids shown at the 50% probability level in accordance with an embodiment of the present disclosure. Selected bond lengths [Å] and angles [°] are as follows: P(1)-C(13): 1.8450; C(13)-C(18): 1.413; C(18)-B(1): 1.560; C(7)-P(1)-C(13): 101.32 (6); C(1)-P(1)-C(13): 101.76 (6); C(18)-C(13)-P(1): 119.85 (10); and C(13)-C(18)-B(1): 126.12 (13).

FIG. 2 is a graph illustrating the Turn-Over Numbers (TON) for the formation of $CH_3OBCat$ in accordance with an embodiment of the present disclosure. More specifically, the $CH_3OBCat$ is obtained from a solution of 2 in benzene-$d_6$ (9 mM) in the presence of 100 equivalents of HBCat under an atmosphere of $CO_2$ (1 atm.): reaction carried out at 23° C. (♦); reaction carried out at 23° C. in presence of two equivalents of HC(O)OMe (▲); reaction carried out at 70° C. (■). The TON's are based on the number of hydrogen atoms transferred to $CO_2$.

DETAILED DESCRIPTION

I. Glossary

Figure 1:
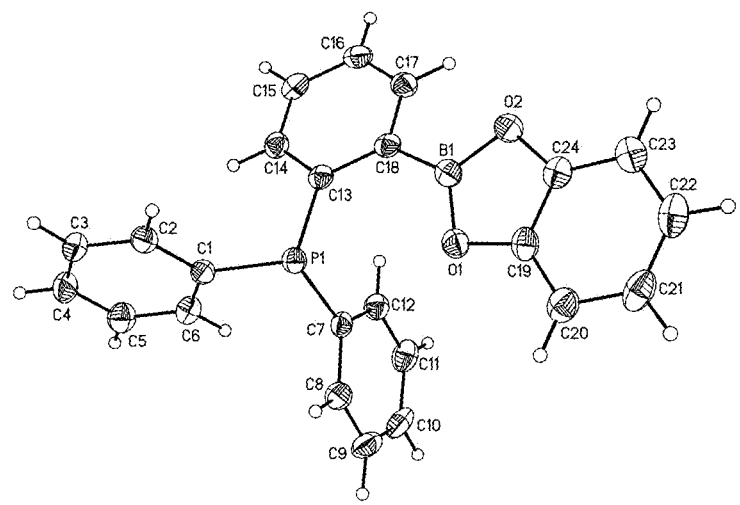

In order to provide a clear and consistent understanding of the terms used in the present disclosure, a number of definitions are provided below. Moreover, unless defined otherwise, all technical and scientific terms as used herein have the same meaning as commonly understood by one of ordinary skill in the art to which this specification pertains.

The word "a" or "an" when used in conjunction with the term "comprising" in the claims and/or the specification may mean "one", but it is also consistent with the meaning of "one or more", "at least one", and "one or more than one" unless the content clearly dictates otherwise. Similarly, the word "another" may mean at least a second or more unless the content clearly dictates otherwise.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±1% of the modified term if this deviation would not negate the meaning of the word it modifies.

As used herein, the term "alkyl" includes both straight-chain and branched. This also applies if they carry substituents or occur as substituents on other residues, for example in alkoxy residues, alkoxycarbonyl residues or arylalkyl residues. Substituted alkyl residues are substituted in any suitable position. Examples of alkyl residues containing from 1 to 10 carbon atoms are methyl, ethyl, propyl, butyl, pentyl, hexyl, heptyl, octyl, nonyl and decyl, the n-isomers of all these residues, isopropyl, isobutyl, isopentyl, neopentyl, isohexyl, isodecyl, 3-methylpentyl, 2,3,4-trimethylhexyl, sec-butyl, tert-butyl, or tert-pentyl. A specific group of alkyl residues is formed by the residues methyl, ethyl, n-propyl, isopropyl, n-butyl, isobutyl, sec-butyl and tert-butyl.

As used herein, the term "cycloalkyl" is understood as being a mono- or bicyclic carbon-based ring system, non-limiting examples of which include cyclopropyl, cyclobutyl, cyclopentyl, cyclohexyl and cycloheptyl.

As used herein, the term "aryl" is understood as being an aromatic substituent which is a single ring or multiple rings fused together and which may optionally be substituted. When formed of multiple rings, at least one of the constituent rings is aromatic. In an embodiment, aryl substituents include phenyl, and naphthyl groups.

The term "substituted" as used herein, means that a hydrogen radical of the designated moiety is replaced with the radical of a specified substituent, provided that the substitution results in a stable or chemically feasible compound. Non-limiting examples of substituents include halogen (F, Cl, Br, or I) for example F, and $C_{1-4}$alkyl.

The term "frustrated Lewis pair" is used herein to refer to a compound or mixture of compounds containing a Lewis acid and a Lewis base which, because of steric hindrance, cannot combine to form a strongly bound adduct, or may not in fact form any adduct at all.

As used herein, the term "Lewis acid" refers to an electron pair acceptor.

As used herein, the term "Lewis base" refers to an electron pair donor.

The term catechol or "CAT" as used herein refers to the group:

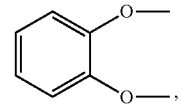

wherein the two oxygen atoms are bonded to two separate atoms (which are the same of or different) or to a single atom.

The term HBPin as used herein refers to pinacolborane.

The term BBN as used herein refers to 9-borabicyclo [3.3.1]nonane.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 99% of the starting material or substrate is converted to product.

II. Preparation of Ambiphilic Catalyst 2—and Use Thereof in the Production of Methanol by Catalytic Reduction of $CO_2$ In a general way, the catalysts corresponding to the compounds of Formula I and II can be prepared and isolated prior to their use in the process according to the general methods described in the literature or using the methods described herein. In an embodiment of the disclosure, formation of the catalyst is performed by reacting a lithiated phosphine with a suitable borane reagent.

The preparation of ambiphilic catalyst 2, in accordance with an embodiment of the present disclosure, is illustrated hereinbelow in Scheme 1.

Scheme 1

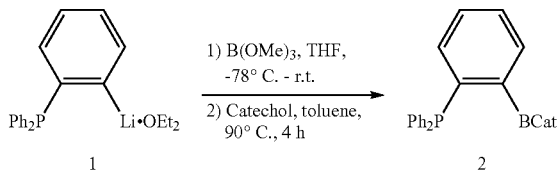

Catecholborane derivative 2 was readily prepared from o-lithiated triphenylphosphine 1 in 80% yield. Multinuclear NMR characterization of derivative 2 demonstrated the species to be monomeric in solution and having no observable P-B interaction. The $^{31}P\{^1H\}$ and $^{11}B\{^1H\}$ NMR chemical shifts were measured to be −4.57 and 33.1 ppm respectively. Furthermore, the solid state structure did not reveal any evidence of P-B interaction which is likely due to the intramolecular distance separating the phosphorus and boron atoms. This is corroborated by the P1-C13-C18 and C13-C18-B1 bond angles, which were measured to be 119.85(10)° and 126.12(13)° respectively (FIG. 1). These values are in close correlation with that expected for a $sp^2$ hybridized carbon (i.e. 120°). Catecholborane derivative 2 was demonstrated to be an active catalyst for the catalytic reduction of carbon dioxide to methanol.

The reaction of 2 under an atmosphere of $CO_2$ (1 atm.) at room temperature resulted in no observable spectroscopic changes in solution (confirmed by $^1H$, $^{31}P$, and $^{11}B$ NMR). Although an adduct between $CO_2$ and 2 could not be observed, the addition of 100 equivalents of HBCat to a solution of 2 in benzene-$d_6$ (9 mM) in a J-Young tube under an atmosphere of $CO_2$ (1 atm.) resulted in the formation of a white precipitate following a reaction period of 24 hours. The precipitate was subsequently identified as being Cat-BOBCat based on a comparison with the independently synthesized product (Scheme 2). Monitoring of the solution by $^1H$ NMR spectroscopy revealed the presence of a new signal at 3.37 ppm, attributed to the presence of $CH_3OBcat$. The hydrolysis of the latter product afforded methanol as characterized by GC-MS. Carrying out the reaction under identical conditions using $^{13}CO_2$ resulted in the formation of $^{13}CH_3OH$.

Scheme 2

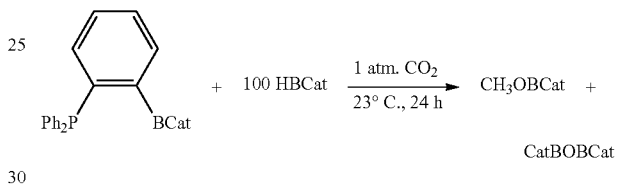

Figure 2:
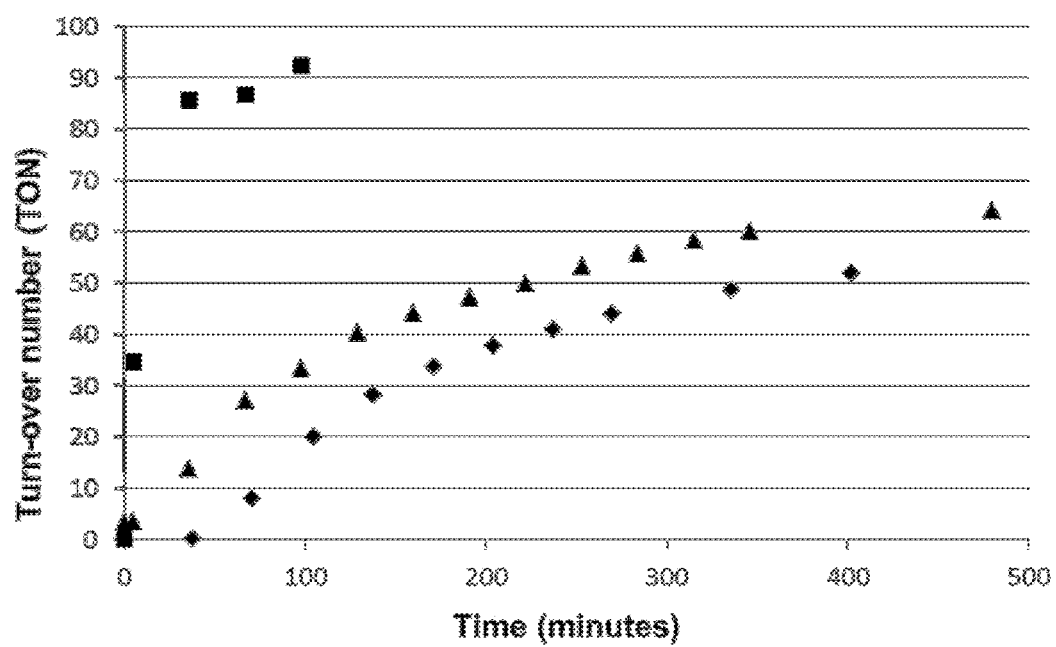

Monitoring the reaction using both $^1H$ and $^{31}P\{^1H\}$ NMR spectroscopy revealed an induction period of 30 minutes in which no spectroscopic changes could be observed. However, after the initial induction period, the reaction starts such that after 2 hours a 34% yield of $CH_3OBCat$ was obtained (FIG. 2, ♦). The observed yield corresponds to a TON of 34 and a TOF of 17 $h^{-1}$. The rate of the reaction diminished as the reaction progressed, suggesting that conversion is dependent on the concentration of HBCat in solution. Indeed, 50% conversion to $CH_3OBcat$ was obtained in less than 5 hours whereas 69% conversion to $CH_3OBcat$ was observed after 24 hours.

The induction period is significantly reduced by the addition of 2 equivalents of methyl formate. In fact, a TON of 40 was observed following a reaction period of 2 hours (FIG. 2, ▲). No significant impact was observed on the reaction rate. The reduction of $CO_2$ also proceeds in the presence of $BH_3.SMe_2$ (100 eq.) as the hydrogen source to generate $(CH_3OBO)_n$. However, a longer induction period is observed (>2 hours). Nonetheless, the formation of the methoxyborane species occurs rapidly once catalysis is initiated. TONs of 108 and 200 were observed following a reaction period of 2 and 5 hours respectively. A TON of 257 was obtained following a reaction period of 14 hours. The greater TON numbers suggest that all hydrogen atoms of $BH_3.SMe_2$ are available for the reduction of $CO_2$.

The temperature has an effect on the efficiency of the catalytic system. Heating a solution comprising 2 and HBCat (100 eq.) under an atmosphere of $CO_2$ (1 atm.) at a temperature of 70° C. resulted in the immediate generation of $CH_3OBCat$ without requiring any induction period (FIG. 2, ■). A TON of 86 was observed following a reaction period of 30 minutes (TOF=172 $h^{-1}$). The TON increased to 92 following a reaction period of 90 minutes. Following a 24 hour reaction period at 70° C. (using a J-Young tube), additional HBCat (100 eq.) was added to the reaction mixture followed by continued heating at 70° C. The catalytic reaction resumed, however with a rate that seemed somewhat slower. This is possibly due to the presence of a large amount of precipitate (CatBOBCat) in the solution, reducing its homogeneity. After an additional 60 minutes of reaction time, following the addition of the further portion of HBCat, an overall TON of 185 was observed. Under similar reaction conditions, $BH_3.SMe_2$ proved to be an excellent hydrogen source, generating $(CH_3OBO)_n$ in less than an hour of reaction time (100% yield and TOF>300 h$^{-1}$). The reaction was similarly carried using other hydroborane sources and the results summarized in Table 1. The addition of HBPin (100 eq.) to a solution of 2 under an atmosphere of $CO_2$ (1 atm.) at 70° C., generated the desired product in 60% yield following a reaction period of 3 hours. The borane reagent HBPin was significantly less active when compared to the HBCat reagent. This observation seems to corroborate the reduced reactivity of HBPin in hydroboration reactions when compared with HBCat. Similarly, a TON of 34 was observed for 9-BBN following a reaction period of 3 hours.

Figure 3:
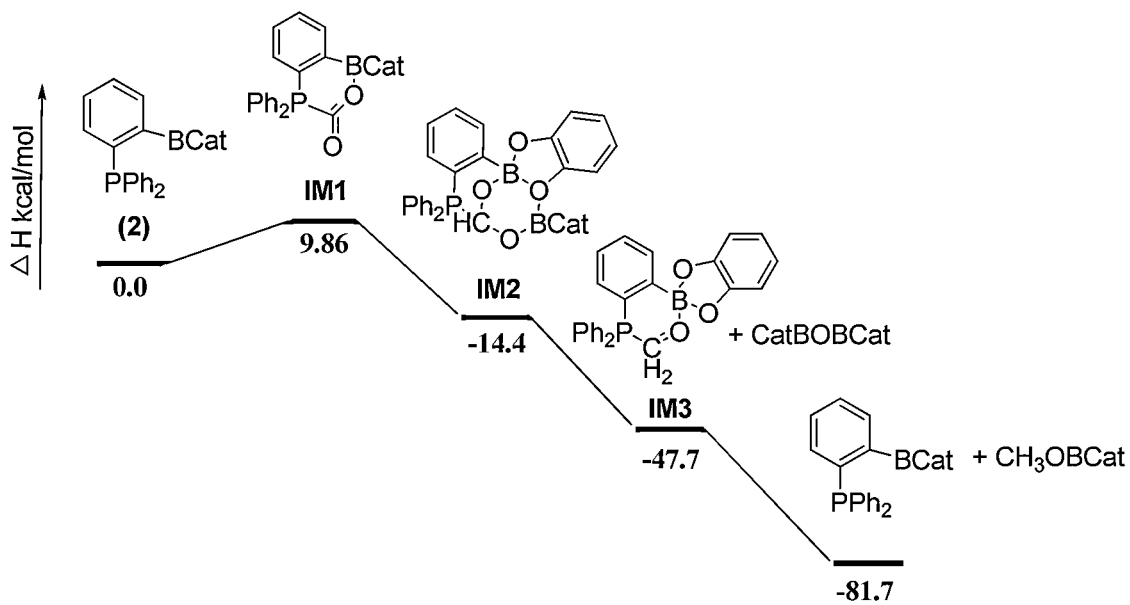
FIG. 3 is an illustration of a calculated theoretical enthalpy profile (in kcal/mol) for the reduction of $CO_2$ by 2 and catecholborane in accordance with an embodiment of the present disclosure.

Density functional theory studies were performed using catecholborane derivative 2 as the catalyst and HBCat as the hydrogen source in order to gain further insight into the reaction mechanism for the catalytic conversion of $CO_2$ into methanol. Only potential intermediates were considered in the study and the results are summarized in FIG. 3. As observed experimentally, the coordination of $CO_2$ with species 2, to generate the corresponding intermediate IM1, is energetically disfavored by 9.86 kcal/mol. This is likely a result of the weak coordination of $CO_2$ with species 2. Indeed, despite the bending of the molecule (indicative of $CO_2$ activation), the C—O bonds appear to be only marginally elongated as compared to free $CO_2$. Nevertheless, adduct IM1 undergoes the addition of an equivalent of HBCat to yield intermediate IM2, whose formation is energetically favored by 14.4 kcal/mol relative to 2. The consumption of a further equivalent of HBCat yields intermediate IM3 and CatBOBCat. The formation of IM3 is also energetically favored by 47.7 kcal/mol relative to 2. The addition of a third equivalent of HBCat regenerates catalyst 2 as well as methanol precursor species $CH_3OBCat$. This last step is energetically favored by a further 34.0 kcal/mol relative to 2. While not wishing to be limited by theory, these results indicate that as soon as the initial coordination of $CO_2$ with 2 has been achieved, the subsequent reduction steps are thermodynamically highly favorable. This study corroborates the initial observation of a rather long induction period for the catalytic reduction process. Although these results show a number of similarities with the formation of $CH_3OSiR_3$ in the $CO_2$ reduction by N-heterocyclic catalysts or to the formation of $CH_2OBR_2$ with a nickel pincer complex, the ambiphilic system shows unique characteristics, notably the stepwise reduction and the three hydride transfers. Indeed, the catalytic system of the present disclosure comprises the activation of the $CO_2$ species, whereas the prior art systems include the activation of the reducing agent. Furthermore, since no trace of HCOOBCat could be observed in solution during the catalytic process, as monitored by $^1$H NMR, suggests that the ambiphilic catalyst remains attached to the reduced carbonyl species, as suggested by the thermodynamic data.

Figure 4:
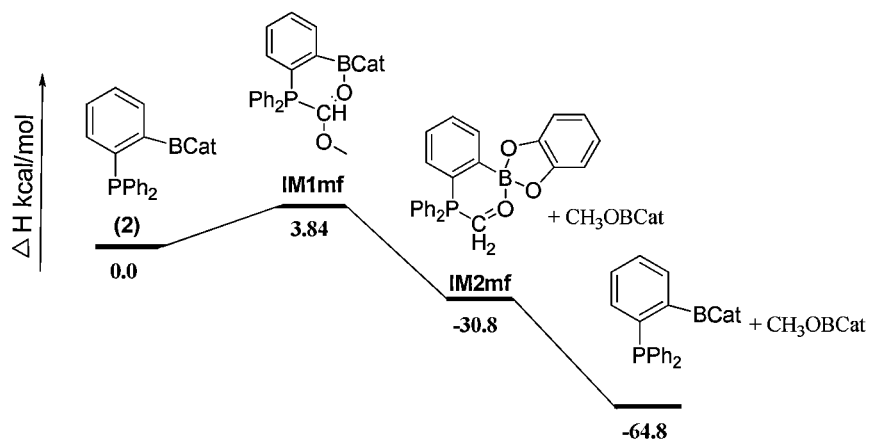
FIG. 4 is an illustration of a calculated theoretical enthalpy profile (in kcal/mol) for the reduction of methylformate by 2 and catecholborane in accordance with an embodiment of the present disclosure.

To confirm these computational results, a further density functional theory study was performed using catecholborane derivative 2 as the catalyst and HBCat as the hydrogen source for the catalytic reduction of methylformate. As for the previous computational study, only potential intermediates were considered and the results are summarized in FIG. 4. The coordination of methylformate with 2 was predicted to result in the formation of intermediate IM1mf. The formation of this intermediate was calculated to be energetically disfavored by 3.84 kcal/mol. When carried out in the absence of HBCat, no trace of intermediate IM1mf could be observed in solution as monitored by $^1$H NMR. However, upon the addition of HBCat to the catalytic system, the conversion to $CH_3OBCat$ could be observed (FIG. 4). This observation confirms that even though the formation of the initial adduct IM1mf is thermodynamically disfavored, the presence of a hydrogen source, such as a hydroborane, is sufficient to push the reaction forward and initiate the reduction process. Furthermore, the reaction does not display any significant induction period, which corroborates the computed thermodynamic preference for the formation of IM1mf over IM1. A similar structure to formaldehyde intermediates IM3 and IM2mf was identified as a key intermediate for both the formation of $CH_3OSiR_3$ in the $CO_2$ reduction by N-heterocyclic catalysts and the formation of $CH_2OBR_2$ with a nickel pincer complex, but could not be observed experimentally. In order to yet further corroborate the proposed reaction mechanism, catecholborane derivative 2 was reacted with paraformaldehyde and heated at 70° C. to provide IM3, which was subsequently identified by multinuclear NMR spectroscopy. The subsequent addition of HBCat to the reaction mixture yielded $CH_3OBCat$. While not wishing to be limited by theory, together, these results suggest the reduction pathway illustrated in Scheme 3, and further suggest that activation of carbon dioxide is the rate limiting step of the catalytic reduction.

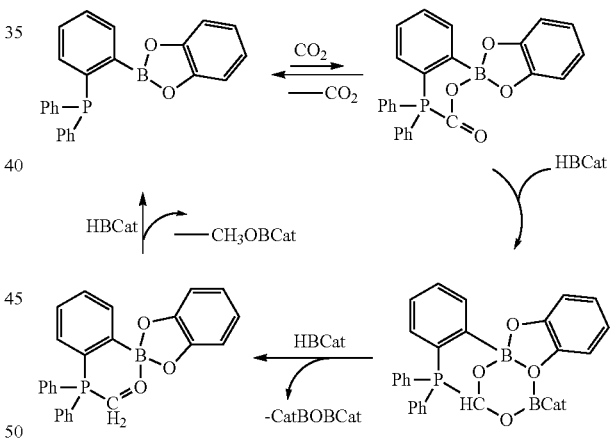

Scheme 3

Figure 6:
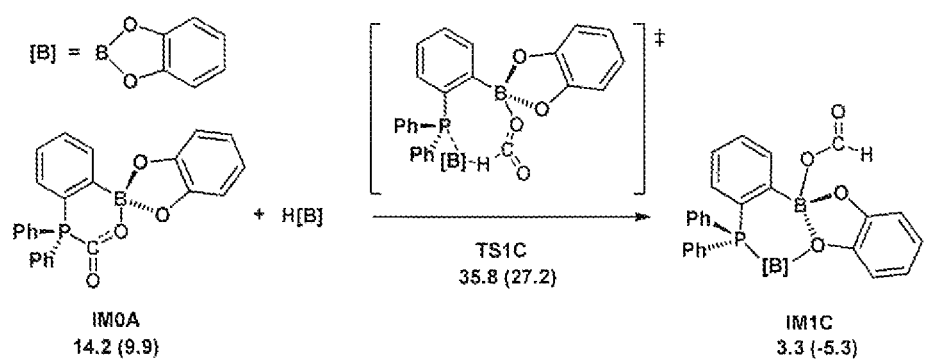
FIG. 6 is an illustration of a theoretical mechanistic pathway for the first reduction step of $CO_2$ to HCOOBCat by 2.

Further theoretical studies have shown that although the catalyst lowers the energy gap for the reduction of $CO_2$ to HCOOBCat, it also plays a significant role in enhancing the rates of the subsequent reduction steps. Moreover, the species in the first reduction step appears to involve the hydridoborato/boronium bifunctional system IM0D. The Lewis base center plays a role in binding carbon dioxide with an ideal geometry, allowing the hydride delivery while the boronium fragment ensures the electrophilic activation of $CO_2$ (TS1D). Compared to the catalyst free reduction, together these factors lead to a lowering of the energy barrier by 6.7 kcal·mol$^{-1}$. A slight increase in energy of only 2.4 kcal·mol$^{-1}$ provides for the possibility of the Lewis acidic site of the catalyst binding $CO_2$, while the phosphine activates the borane for delivery of a hydride to the electrophilic carbon of $CO_2$ (TS1C) (FIG. 6). Both pathways put emphasis on the fact that the role of the catalyst appears to be the simultaneous activation of both reagents (the borane reagent and $CO_2$) as opposed to the activation of $CO_2$ alone.

Figure 5:
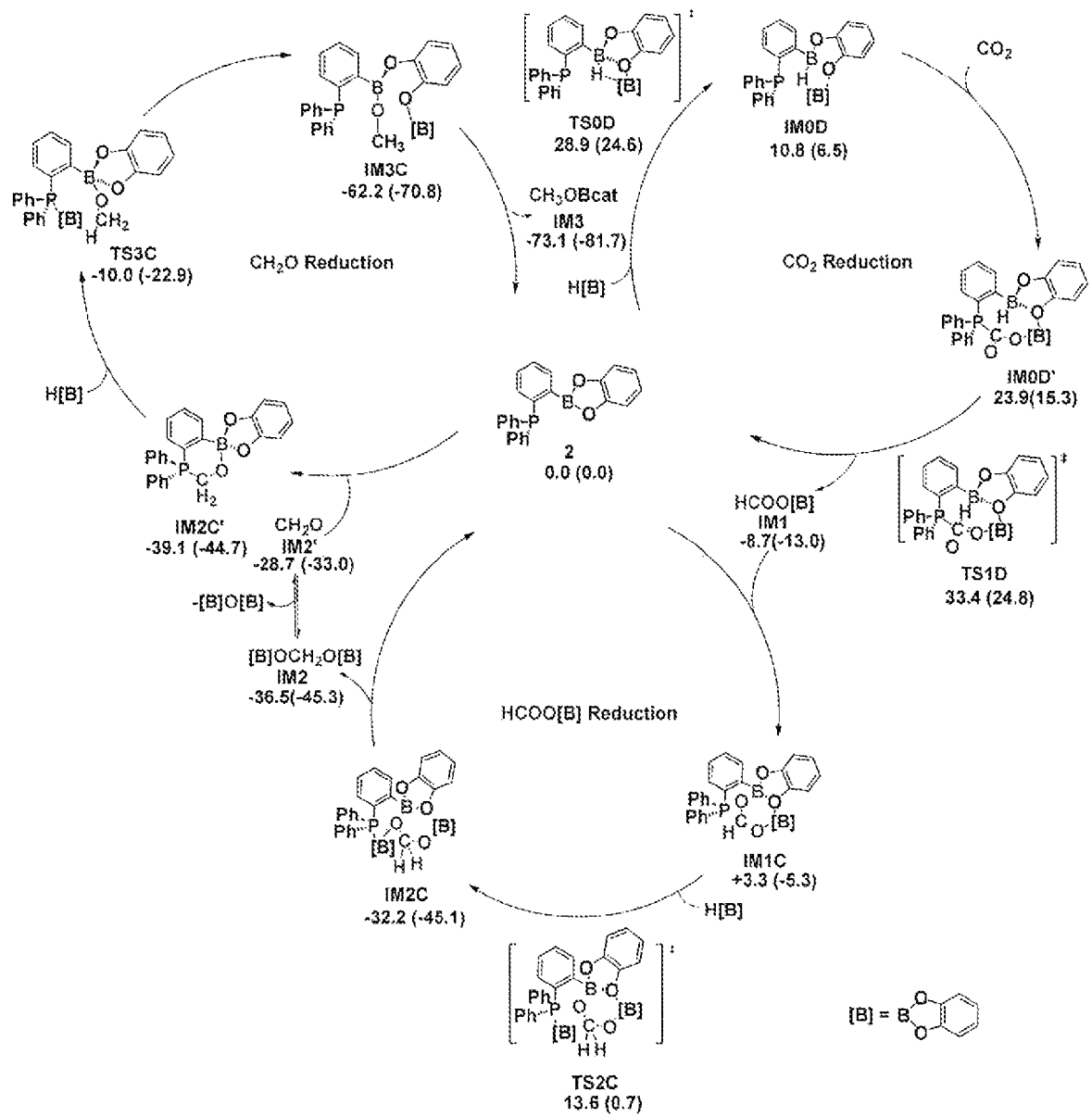
FIG. 5 is an illustration of a theoretical mechanistic pathway for the reduction of $CO_2$ to $CH_3OBCat$ by 2.

The reduction of both HCOOBCat and $CH_2O$ was shown to be possible without any implication from the catalyst and consequently, some of these reductions are expected to occur catalyst-free in the presence of a large excess of HBCat. However, activation of the HBCat moiety by the Lewis base center while the substrate is fixed and activated by the Lewis acidic boron center results in lowering the transition state energies by 11.1 and 2.3 kcal·mol for the hydroboration of HCOOBCat and $CH_2O$, respectively (TS2C and TS3C respectively). The rapid reduction of HCOOBCat by the catalyst explains why it could not be observed experimentally. On the other hand, the 14.7 kcal·mol$^{-1}$ bonding interaction of the catalyst with formaldehyde (IM2C') rationalizes the fact that this particular adduct can be observed spectroscopically during catalysis. The entire catalytic process is summarized and illustrated in FIG. 5.

These results are indicative of the importance of designing FLPs that incorporate a moderate Lewis base and Lewis acid pair. Indeed, a moderate Lewis base would not induce strong binding of $CO_2$ which might hinder the hydride transfer or generate stable adducts with the intermediates. Similarly, a moderate Lewis acid would allow for the release of the various hydroboration products from the catalyst into the reaction medium. Furthermore, the presence of both the Lewis acid and Lewis base in a single molecule reduces the entropic cost associated with the catalyzed steps.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES 1. (a) T. Matsuo, H. Kawaguchi, *J. Am. Chem. Soc.* 2006, 128, 12362-12363; (b) S. Park, D. Bézier, M. Brookhart, *J. Am. Chem. Soc.* 2012, 134, 11404-11407; (c) S. J. Mitton, L. Turculet, *Chem. Eur. J.* 2012, 48, 15258-15262; (d) A. Berkefeld, W. E. Piers, M. Parvez, L. Castro, L. Maron, O. Eisenstein. *Chem. Sci.* 2013, 4, 2152-2162.
2. R. Lalrempuia, M. Iglesias, V. Polo, P. J. Sanz Miguel, F. J. Fernandez-Alvarez, J. Pérez-Torrente, L. A. Oro. *Angew. Chem. Int. Ed.* 2012, 51, 12824-12827.
3. T. Eisenschmid, Eisenberg. C. R, *Organometallics* 1989, 8, 1822-1824.
4. (a) S. Chakraborty, J. Zhang, J. A. Krause, H. Guan. *J. Am. Chem. Soc.* 2010, 132, 8872-8873; (b) F. Huang, C. Zhang, J. Jiang, Z. Wang, H. Guan *Inorg. Chem.* 2011, 50, 3816-3825; (c) S. Chakraborty, Y. J. Patel, J. A. Krause, H. Guan, *Polyhedron* 2012, 32, 30-34; (d) S. Bontemps, L. Vendier, S. Sabo-Etienne, *Angew. Chem. Int. Ed.* 2012, 51, 1671-1674.
5. (a) K. Tominaga, Y. Sasaki, M. Kawai, T. Watanabe, M. J. Saito, *Chem. Soc. Chem. Commun.* 1993, 629-631; (b) C. A. Huff, M. S. Sanford, *J. Am. Chem. Soc.* 2011, 133, 18122-18125; (c) S. Wesselbaum, T. vomStein, J. Klankermayer, W. Leitner, *Angew. Chem. Int. Ed.* 2012, 51, 7499-7502.
6. E. Balaraman, C. Gunanathan, J. Zhang, L. J. W. Shimon, D. Milstein, *Nat. Chem.* 2011, 3, 609-614.
7. (a) A. Berkefeld, W. E. Piers, M. Parvez, *J. Am. Chem. Soc.* 2010, 132, 10660-10661; (b) M. Khandelwal, R. J. Wehmschulte, *Angew. Chem.* 2012, 124, 7435-7439.
8. (a) S. N. Riduan, Y. Zhang, J. Y. Ying. *Angew. Chem., Int. Ed.* 2009, 48, 3322-3325; (b) F. Huang, G. Lu, L. Zhao, H. Li, Z. X. Wang, *J. Am. Chem. Soc.* 2010, 132, 12388-12396; (c) A. Schäfer, W. Saak, D. Haase, and T. Müller, *Angew. Chem. Int. Ed.* 2012, 51, 2981-2984.
9. (a) C. M. Mömming, E. Otten, G. Kehr, R. Fröhlich, S. Grimme, D. W. Stephan, G. Erker. *Angew. Chem. Int. Ed.* 2009, 48, 6643-6646; (b) J. Boudreau, M-A. Courtemanche, F-G. Fontaine, *Chem. Commun,* 2011, 47, 11131-11133; (c) E. Theuergarten, J. Schlösser, D. Schlüns, M. Freytag, C. G. Daniliuc, P. G. Jones and M. Tamm, *Dalton Trans.,* 2012, 41, 9101; (d) S. Roters, C. Appelt, H. Westenberg, A. Hepp, J. C. Slootweg, K. Lammertsma and W. Uhl. *Dalton Trans.,* 2012, 41, 9033; (e) C. Appelt, H. Westenberg, F. Bertini, A. W. Ehlers, J. C. Slootweg, K. Lammertsma, W. Uhl, *Angew. Chem. Int. Ed.* 2011, 50, 3925-3928.
10. (a) G. Ménard, D. W. Stephan, *J. Am. Chem. Soc.* 2010, 132, 1796-1797; (b) A. E. Ashley, A. L. Thompson. D. O'Hare, *Angew. Chem., Int. Ed.* 2009, 48, 9839-9843.
11. (a) S. Bontemps, G. Bouhadir, D. C. Apperley, P. W. Dyer, K. Miqueu, D. Bourissou, *Chem. Asian J.* 2009 428-435; (b) S. Bontemps, G. Bouhadir, K. Miqueu, D. Bourissou, *J. Am. Chem. Soc.* 2006 128, 12056-12057.
12. O. Baslé, S. Porcel, S. Ladeira, G. Bouhadirand, D. Bourissou. *Chem. Commun.,* 2012, 48, 4495-4497.
13. S. Porcel, G. Bouhadir, N. Saffon, L. Maron and D. Bourissou, *Angew. Chem., Int. Ed.,* 2010, 49, 6186.

TABLE 1

Reaction Conditions and TONs for the Catalytic Reduction of $CO_2$ Using Various Hydroboranes.$^a$

| Entry | Borane | # eq. | Time (h) | Temp (° C.) | TON$^b$ |
|-------|--------|-------|----------|-------------|---------|
| 1 | HBCat | 100 | 36 | 70 | 86 |
| 2 | HBCat | 100 | 98 | 70 | 92 |
| 3 | HBCat | 100 + 100$^d$ | 30 | 70 | 136 |
| 4 | HBCat | 100 + 100$^d$ | 60 | 70 | 185 |
| 5 | HBPin | 100 | 174 | 70 | 60 |
| 6 | 9-BBN$^e$ | 50$^e$ | 174 | 70 | 34 |
| 7 | HBBz | 100 | 1440 | 70 | 0 |

$^a$Reaction conditions: 2.0 mg (0.0053 mmol) of 2 in 0.6 mL of benzene-d$_6$.
$^b$Based on mole of B-H consumed per mole of 2 (determined by $^1$H NMR integration using hexamethylbenzene as internal standard).
$^c$2.0 equiv. (0.0106 mmol) of HCOOMe were added.
$^d$A second addition of 100 equivalents of HBCat was carried out 24 hours after the first addition.
$^e$Limited at 50 equivalents because of low solubility of 9-BBN.

What is claimed is:

1. A catalyst for the reduction of $CO_2$, where the catalyst is represented by Formula I:

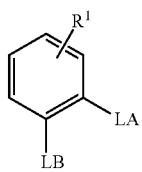

Formula I wherein:
LB is a Lewis base of formula $PR^2R^3$;
LA is a Lewis acid of formula $BR^4R^5$;
$R^1$ is selected from hydrogen, alkyl, substituted alkyl, cycloalkyl, substituted cycloalkyl, phenyl and substituted phenyl;
$R^2$ and $R^3$ are independently selected from alkyl, substituted alkyl, cycloalkyl, substituted cycloalkyl, phenyl and substituted phenyl;
$R^4$ and $R^5$ are connected together by an —O—B—O— bridge to form, together with the carbon atoms to which they are attached, a 7-, 8- or 9-membered mono or bicyclic ring system or a substituted 7-, 8- or 9-membered mono or bicyclic ring system.

2. The catalyst of claim 1, wherein $PR^2R^3$ is selected from:

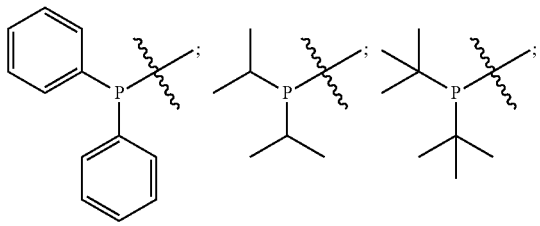

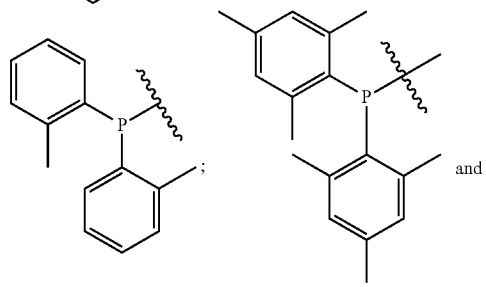

and

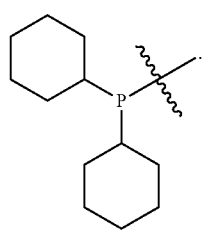

3. The catalyst of claim 1, wherein $BR^4R^5$ is:

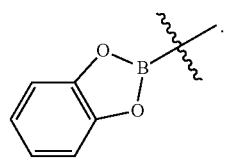 [SMILES: *B1Oc2ccccc2O1]

4. The catalyst of claim 1, having the structure:

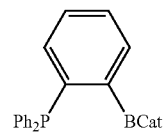

wherein Cat is a catechol group.

5. A process for the production of methanol from $CO_2$, the process comprising:
combining a catalyst of claim 1 and a hydrogen source to produce a mixture;
exposing the mixture to $CO_2$ under conditions to convert the $CO_2$ into methoxyboranes; and
hydrolyzing the methoxyboranes to produce methanol.

6. The process of claim 5, wherein the hydrogen source is a hydroborane.

7. The process of claim 6, wherein the hydroborane is selected from the group consisting of HBCat, HBPin, 9-BBN and $BH_3$—$SMe_2$.

8. A catalyst for the reduction of $CO_2$, having the Formula:

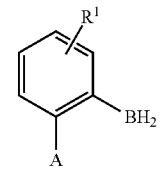

wherein:
A is $PR^2R^3$; and
$R^1$ is selected from hydrogen, alkyl, substituted alkyl, cycloalkyl, substituted cycloalkyl, phenyl and substituted phenyl; and
$R^2$ and $R^3$ are independently selected from alkyl, substituted alkyl, cycloalkyl, substituted cycloalkyl, phenyl and substituted phenyl.

9. A molecule having the formula:

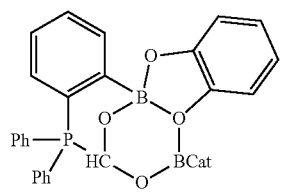

wherein Cat is a catechol group.

* * * * *